(12) United States Patent
Yun et al.

(10) Patent No.: US 10,716,749 B2
(45) Date of Patent: Jul. 21, 2020

(54) METHODS AND COMPOSITIONS FOR TREATING A RENAL DISEASE CONDITION IN A SUBJECT

(75) Inventors: Anthony Joonkyoo Yun, Palo Alto, CA (US); Patrick Yuarn-Bor Lee, Menlo Park, CA (US)

(73) Assignee: Palo Alto Investors, Palo Alto, CA (US)

( * ) Notice: Subject to any disclaimer, the term of this patent is extended or adjusted under 35 U.S.C. 154(b) by 1610 days.

(21) Appl. No.: 11/592,027

(22) Filed: Nov. 1, 2006

(65) Prior Publication Data
US 2007/0112327 A1 May 17, 2007

Related U.S. Application Data

(60) Provisional application No. 60/733,433, filed on Nov. 3, 2005.

(51) Int. Cl.
*A61K 9/00* (2006.01)
*A61N 1/36* (2006.01)

(52) U.S. Cl.
CPC ........ *A61K 9/0034* (2013.01); *A61N 1/36007* (2013.01)

(58) Field of Classification Search
USPC .......................... 604/20, 500, 890.1; 607/2, 3
See application file for complete search history.

(56) References Cited

U.S. PATENT DOCUMENTS

| | | | | |
|---|---|---|---|---|
| 4,003,379 A | * | 1/1977 | Ellinwood, Jr. | A61B 5/0468 128/DIG. 1 |
| 4,885,173 A | * | 12/1989 | Stanley et al. | 424/440 |
| 4,923,874 A | * | 5/1990 | McMahon et al. | 514/261.1 |
| 5,262,421 A | * | 11/1993 | Su et al. | 514/280 |
| 5,338,726 A | * | 8/1994 | Shiosaki et al. | 514/17 |
| 5,338,744 A | * | 8/1994 | Dudley et al. | 514/303 |
| 5,688,770 A | * | 11/1997 | Watkins | A61K 38/553 514/15.8 |
| 5,694,950 A | * | 12/1997 | McMichael | A61K 49/0004 128/898 |
| 5,782,874 A | * | 7/1998 | Loos | 607/2 |
| 5,807,895 A | * | 9/1998 | Stratton et al. | 514/573 |
| 5,859,043 A | * | 1/1999 | Kapusta | 514/409 |
| 6,073,048 A | * | 6/2000 | Kieval et al. | 607/17 |
| 6,086,527 A | | 7/2000 | Talpade | |

(Continued)

OTHER PUBLICATIONS

"Fenoldopam Mesylate for the Prevention of Contrast-Induced Nephropathy: A Randomized Controlled Trial." JAMA. 2003;290(17):2284-2291.*

(Continued)

*Primary Examiner* — Scott J Medway
(74) *Attorney, Agent, or Firm* — Bret E. Field; Bozicevic, Field & Francis LLP

(57) ABSTRACT

Methods for treating a renal associated disease condition in a subject are provided. The subject methods are characterized by modulating at least one portion of the subject's autonomic nervous system in a manner effective to treat a renal condition in the subject. Specifically, the methods may include modulating, e.g., increasing, a parasympathetic/sympathetic activity ratio in the subject. Also provided are compositions, kits and systems for practicing the subject methods.

19 Claims, 1 Drawing Sheet

(56) References Cited

U.S. PATENT DOCUMENTS

| | | | | |
|---|---|---|---|---|
| 6,323,236 | B2* | 11/2001 | McElroy | A61K 31/18 514/439 |
| 6,447,443 | B1* | 9/2002 | Keogh et al. | 600/37 |
| 6,522,926 | B1* | 2/2003 | Kieval et al. | 607/44 |
| 6,615,081 | B1* | 9/2003 | Boveja | 607/2 |
| 6,845,267 | B2* | 1/2005 | Harrison et al. | 607/3 |
| 6,978,174 | B2 | 12/2005 | Gelfand et al. | |
| 7,072,711 | B2* | 7/2006 | Girouard et al. | 607/3 |
| 7,079,888 | B2* | 7/2006 | Oung et al. | 600/513 |
| 7,117,034 | B2* | 10/2006 | Kronberg | A61N 1/326 607/2 |
| 7,162,303 | B2* | 1/2007 | Levin et al. | 607/44 |
| 7,252,971 | B2* | 8/2007 | Benson et al. | 435/69.1 |
| 7,363,076 | B2* | 4/2008 | Yun et al. | 607/3 |
| 2003/0216792 | A1 | 11/2003 | Levin et al. | |
| 2004/0111033 | A1* | 6/2004 | Oung | A61B 5/02405 600/483 |
| 2004/0167415 | A1* | 8/2004 | Gelfand | A61B 17/12036 600/500 |
| 2005/0137626 | A1* | 6/2005 | Pastore et al. | 607/3 |
| 2005/0192638 | A1 | 9/2005 | Gelfand et al. | |
| 2005/0228459 | A1 | 10/2005 | Levin et al. | |
| 2005/0228460 | A1 | 10/2005 | Levin et al. | |
| 2005/0234523 | A1 | 10/2005 | Levin et al. | |
| 2005/0245535 | A1* | 11/2005 | Hangeland et al. | 514/252.12 |
| 2005/0267010 | A1 | 12/2005 | Goodson et al. | |
| 2005/0288730 | A1 | 12/2005 | Deem et al. | |
| 2006/0025821 | A1 | 2/2006 | Gelfand et al. | |
| 2006/0041277 | A1 | 2/2006 | Deem et al. | |
| 2006/0116721 | A1 | 6/2006 | Yun et al. | |

OTHER PUBLICATIONS

Dupont, "Carvedilol and the kidney." Journal of Molecular Medicine. vol. 7, Supp. 2 (1992).*

Pilz, Bernhard et al. "Aliskiren, a Human Renin Inhibitor, Ameliorates Cardiac and Renal Damage in Double-Transgenic Rats." Hypertension 46 (2005): 569-76.*

Stanton, Alice et al. "Blood Pressure Lowering in Essential Hypertension With an Oral Renin Inhibitor, Aliskiren." Hypertension 42 (2003): 1137-43.*

N. Parekh. "A novel method for infusing drugs continuously into the renal artery of rats." AJP—Renal Physiology, vol. 268, Issue 5 967-F971 (1995).*

Doohan, James. "Cardiac Output." Santa Barbara City College (2000). Online: http://www.biosbcc.net/doohan/sample/htm/COandMAPhtm.htm.*

Weber et al. "Comparison of the hemodynamic effects of metoprolol and carvedilol in hypertensive patients." Cardiovasc Drugs Ther. May 1996;10(2):113-7. Online: <http://www.ncbi.nlm.nih.gov/pubmed/8842502>.*

"Treat". Merriam-Webster Dictionary. Accessed online, 2012. <<http://www.merriam-webster.com/dictionary/treat>>.*

Bertram Katzung. "Basic & Clinical Pharmacology: Edition 9". McGraw Hill Professional. Jan. 5, 2004. Online: <http://www.bionica.info/biblioteca/katzungbasicclinicalpharmacology.pdf>.*

Tumlin et al. "Fenoldopam mesylate blocks reductions in renal plasma flow after radiocontrast dye infusion: A pilot trial in the prevention of contrast nephropathy." 143: 5. 2002. pp. 894-903.*

"Parasympathomimetic drug." Wikipedia. Accessed Feb. 22, 2016. Online: <https://en.wikipedia.org/wiki/parasympathomimetic_drug>.*

"Sympatholytic." Wikipedia. Accessed Feb. 22, 2016. Online: <https://en.wikipedia.org/wiki/Sympatholytic>.*

Tublin et al. "Current Concepts in Contrast Media-Induced Nephropathy." AJR 1998. 171. pp. 933-939.*

Taylor et al. "Prolonged Fenoldopam Infusions in Patients With Mild to Moderate Hypertension." AJH 1999;12: pp. 906-914.*

"Metoprolol." Wikipedia. Accessed Feb. 22, 2016. Online: <https://en.wikipedia.org/wiki/Metoprolol>.*

Poole et al. "Pharmacotherapeutics for Advanced Practice: A Practical Approach." 2nd ed. Lippincott, Williams and Wilkins. 2006. pp. 205-207.*

Kobrin S, Aradhye S. Preventing progression and complications of renal disease. Quadrant Health Com, Inc. Hospital Medicine. 1997;33[11]:11-12. 17-18, 20, 29-31, 35-36, 39-40. Accessed online: <http://www.newmanveterinary.com/Humans-Treatment%20of%20Renal%20Failure%20Medscape.htm>.*

* cited by examiner

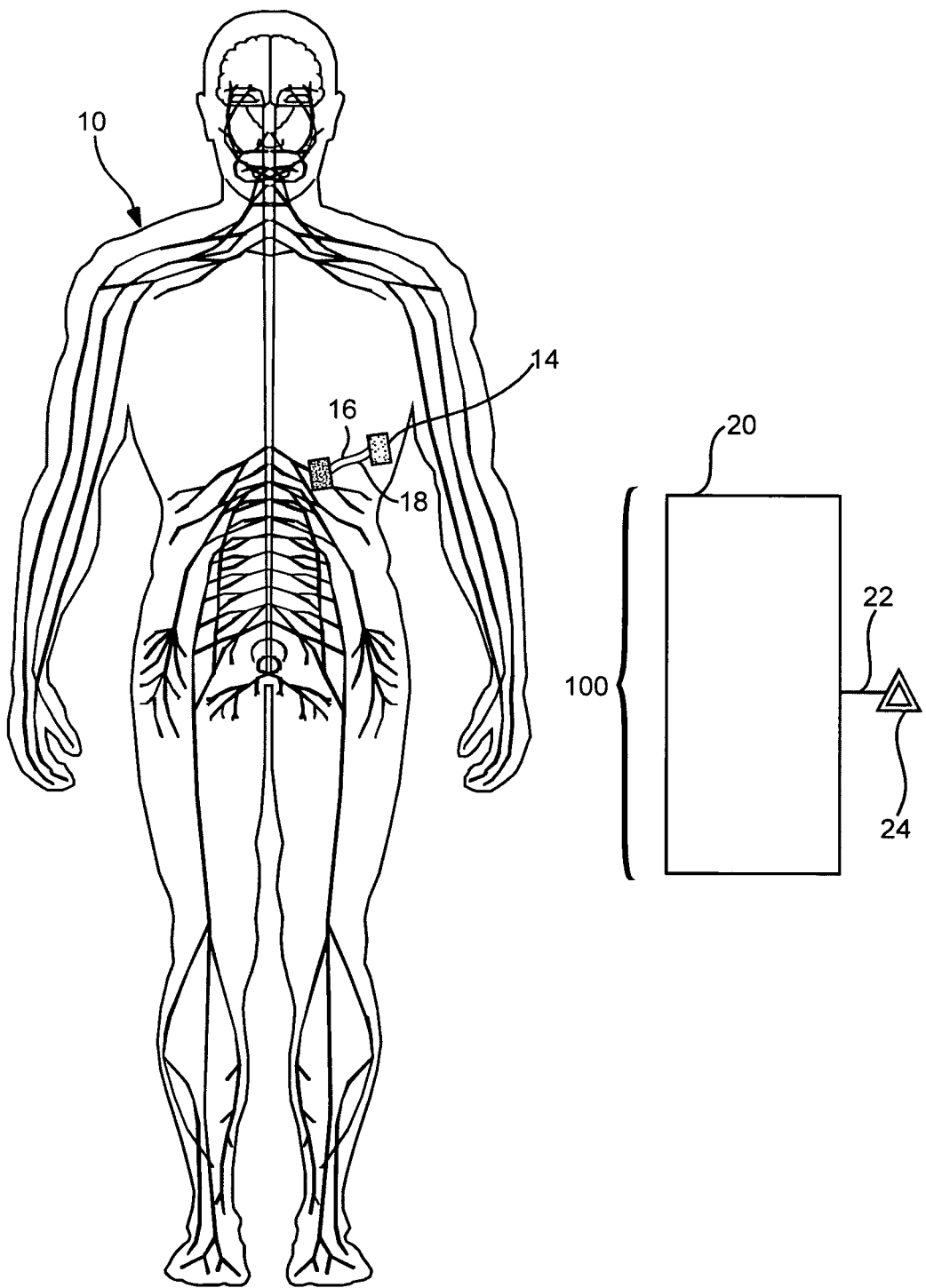

METHODS AND COMPOSITIONS FOR TREATING A RENAL DISEASE CONDITION IN A SUBJECT

CROSS-REFERENCE TO RELATED APPLICATIONS

Pursuant to 35 U.S.C. § 119 (e), this application claims priority to the filing date of U.S. Provisional Patent Application Ser. No. 60/733,433 filed Nov. 3, 2005; the disclosure of which application is herein incorporated by reference.

INTRODUCTION

The kidney is made up of about a million tiny units called nephrons. The nephron is where blood carrying capillaries intertwine with tiny waste-processing tubules. A complicated chemical exchange takes place in the nephron where waste materials and water leave the blood via the capillaries and enter the urinary system via the tubules. Every day a person's kidneys sift out about 2 quarts of waste products and excess water from the blood. On average the kidneys process about 200 quarts of blood. The waste and extra water become urine, which typically flows through the ureters to the bladder.

Extreme trauma may result in the loss of kidney function. This loss of function results in the retention of excess fluids within the kidneys and the build up of waste products, such as nitrogen. When the kidneys stop working over a period of hours, days, or weeks renal failure results. The most common causes of acute forms of renal failure include dehydration, direct trauma to the kidneys, decreased cardiac output, blood loss, and various medications; such as contrast agents used in X-ray tests, nonsteroidal anti-inflammatory drugs (NSAIDs), and antibiotics. During renal failure excess fluids are not removed by the kidneys and the body's normal chemical balance is upset as chemicals and electrolytes, such as sodium, potassium, and calcium, build up to abnormally high levels and become toxic to the body.

The treatment of renal failure typically depends on the underlying cause of the kidney failure. For instance, where the underlying cause of failure is due to dehydration or loss of blood, the resultant treatment may involve the replacement of the lost fluids, such as water, blood, and plasma, and the restoration of blood flow to the kidneys. Where the underlying cause is due to the administration of various medications, the resultant treatment may involve the discontinuation of such medications. However, in many circumstances these treatments may involve procedures requiring blood transfusions, plasma exchange, the discontinuation of needed medicaments, and may require more invasive procedures such as the use of a catheter (for excess fluid removal), dialysis, and even kidney transplantation.

Accordingly, there is a continued need for the development of new therapeutic modalities for the treatment of renal conditions.

SUMMARY

Methods for treating a renal associated disease condition in a subject are provided. The subject methods are characterized by modulating at least one portion of the subject's autonomic nervous system in a manner effective to treat a renal condition in the subject. Specifically, the methods may include modulating, e.g., increasing, a parasympathetic/sympathetic activity ratio in the subject. Also provided are compositions, kits and systems for practicing the subject methods.

BRIEF DESCRIPTIONS OF THE DRAWINGS

FIG. 1 shows an exemplary embodiment of an electric energy applying device operatively positioned in a subject's body in accordance with embodiments of the subject methods.

DETAILED DESCRIPTION

Methods for treating a renal associated disease condition in a subject are provided. The subject methods are characterized by modulating at least one portion of the subject's autonomic nervous system in a manner effective to treat a renal condition in the subject. Specifically, the methods may include modulating, e.g., increasing, a parasympathetic/sympathetic activity ratio in the subject. Also provided are compositions, kits and systems for practicing the subject methods.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods of Treatment

Aspects of the invention include methods of treating a disease condition in a subject. In the subject methods, a disease condition, such as a renal condition, is treated by modulating at least one portion of the autonomic nervous system. Specifically, the methods include modulating a parasympathetic/sympathetic activity ratio in the subject. In certain embodiments the parasympathetic/sympathetic activity ratio is increased. For instance, the parasympathetic/sympathetic activity ratio in a subject may be increased by administering an effective amount of a pharmacological agent, applying electrical energy to the subject, or both, so as to treat the disease condition. Also provided are compositions, systems, and kits that find use in practicing the subject methods.

In certain embodiments, the disease condition is a renal associated condition, for instance, a renal condition such as chronic renal failure, acute renal failure, contrast nephropathy (e.g., iodine-based contrast nephropathy), cardiorenal syndrome, nephropathy and the like. In certain embodiments, the renal condition is manifested by an increase in a hormone level, such as an increase in rennin, angiotensin, aldosterone, vasopressin, catecholamines, natriuretic peptides, and the like, and treatment involves the reduction of the indicative hormone level.

Modulation of the autonomic nervous system may be accomplished using any suitable method, including employing electrical, thermal, vibrational, magnetic, acoustic, baropressure, optical, or other sources of energy to modulate autonomic balance, where in representative embodiments modulation is achieved via pharmacological modulation and/or electrical energy modulation in a manner that is effective to treat a subject for a renal condition. Certain embodiments include pharmacologically or electrically modulating at least a portion of a subject's autonomic nervous system, e.g., that portion associated with the kidney, e.g., that directly or indirectly modulates the autonomic activity of the kidney, e.g., by decreasing and/or increasing parasympathetic and/or sympathetic activity in at least a portion of the subject's autonomic nervous system. In certain embodiments, modulation may include increasing the parasympathetic activity/sympathetic activity ratio in at least a portion of the subject's autonomic nervous system. In certain embodiments, modulation may include increasing the sympathetic activity/parasympathetic activity ratio in at least a portion of the subject's autonomic nervous system. In certain embodiments, both electrical and pharmacological modulation are employed.

As will be described in greater detail below, in certain embodiments the modulation of the autonomic nervous system may affect central motor output and/or nerve conduction and/or transmitter release and/or synaptic transmission and/or receptor activation, and in representative embodiments is a change that provides an increase in the parasympathetic activity/sympathetic activity ratio (as used herein, "activity" and "function' are used interchangeably).

For example, at least a portion of the autonomic nervous system may be modulated to alter, shift or change parasympathetic activity and/or sympathetic activity from a first state to a second state, where the second state is characterized by an increase in the parasympathetic activity/sympathetic activity ratio relative to the first state. Accordingly, embodiments of the subject invention include modulating at least a portion of a subject's autonomic nervous system to increase the parasympathetic activity/sympathetic activity ratio, i.e., to increase parasympathetic activity relative to sympathetic activity so as to treat a subject for a renal associated condition. Increasing the parasympathetic activity/sympathetic activity ratio may be achieved by stimulating the parasympathetic system to increase activity in at least a portion of the parasympathetic system, e.g., stimulating at least one parasympathetic nerve fiber.

Alternatively or in addition to stimulating at least one parasympathetic nerve fiber to increase activity, increasing the parasympathetic activity/sympathetic activity ratio may be achieved by inhibiting activity in the sympathetic system, e.g., inhibiting activity in at least one sympathetic nerve fiber to achieve an increased parasympathetic activity relative to sympathetic activity. Still further, in certain embodiments the subject invention provides methods of both increasing activity in at least one parasympathetic nerve fiber and inhibiting activity in at least one sympathetic nerve fiber to achieve the desired result.

By "increased ratio of parasympathetic activity to sympathetic activity" and analogous terms is meant that this ratio is increased in at least a portion of the autonomic nervous system, where the increase is at least great enough to treat a given condition. As will be described in greater detail below, while the ratio of sympathetic function/parasympathetic function may be increased according to embodiments of the subject invention to treat a subject for a condition, such as a renal condition, the net result may be a parasympathetic bias (i.e., parasympathetic dominance), a sympathetic bias (i.e., sympathetic dominance), or the activities of the sympathetic system and parasympathetic system may be substantially equal (i.e., neither is dominant).

By "bias" is meant that the particular "biased" component of the autonomic nervous system has a higher activity level than the other component. For example, a parasympathetic bias refers to a higher level of parasympathetic activity than sympathetic activity, and vice versa, where such bias may be systemic or localized. The net result of the subject methods to treat a condition may be higher or greater parasympathetic activity relative to sympathetic activity in at least the area of the autonomic system targeted or rather in need of modulation, higher or greater sympathetic activity relative to parasympathetic activity in at least the area of the autonomic system targeted or rather in need of modulation, or substantially equal activity levels of sympathetic activity and parasympathetic activity.

For example, embodiments of the subject methods may include treating a subject for sympathetic bias and/or a renal associated condition by administering an effective amount of an anti-adrenergic agent and/or applying an appropriate electrical stimulation to the subject, where the administered agent or electrical stimulus may result in a parasympathetic bias or substantially equivalent activity levels of parasympathetic activity and sympathetic activity.

The pharmacological and/or electrical modulation may provide an increase in function of at least a portion of the autonomic system, e.g., increase function in at least one parasympathetic nerve fiber, and/or provide a decrease in function or dampening of a portion of the autonomic system, e.g., may inhibit activity in at least one sympathetic nerve fiber or inhibit nerve pulse transmission. The modulation may be systemic or regional (i.e., localized). In other words, the entire autonomic nervous system may be modulated (e.g., the entire sympathetic nervous system and/or parasympathetic nervous system may be modulated) or only a portion of the autonomic nervous system may be modulated (e.g., only a portion of the sympathetic nervous system and/or parasympathetic nervous system may be modulated). Localization may be with respect to a particular area, organ, e.g., kidney, or even to a particular nerve fiber. For example, localization may be with respect to innervations of one or more organs. Area(s) of the autonomic nervous system may include, but are not limited to, pre- and post ganglionic nerve fibers, ganglionic structures, efferent and afferent nerve fibers, the hypothalamus, receptors on the hypothalamus, afferent autonomic nerves (sympathetic and parasympathetic) and hormonal receptors on the hypothalamus. In certain embodiments, a given nerve fiber or the like may be modulated with respect to sympathetic and/or parasympathetic activity in more than one area of the nerve fiber.

In certain embodiments, the parasympathetic/sympathetic activity ratio of kidneys is selectively increased. By selectively increased is meant that the activity ratio or bias of the kidneys is modulated to at least to a greater extent than other regions of the body, such that the ratio or bias is not systemically modulated. In certain of these embodiments, selectively increase the ratio or bias of the kidneys comprises exclusively modulating the ratio or bias of these organs, to the exclusion of other parts of the body. Selective modulation may be achieved using any convenient protocol, e.g., by selectively stimulating or pacing autonomic nerves innervating the kidneys, by selectively delivering pharmacological agents to the kidneys, etc. As such, representative embodiments of the invention are characterized in that the parasympathetic/sympathetic activity ratio of the kidney(s) is modulated, e.g. using any of a variety of methods described in this application.

Methods and devices for treating a subject for a condition by modulating at least a portion of the subject's autonomic nervous system have been described in copending, commonly assigned U.S. patent application Ser. No. 10/661,368, the disclosure of which is herein incorporated by reference. Briefly, in accordance with the subject invention to treat a subject for a renal condition, at least a portion of the autonomic nervous system may be modulated using any suitable technique, including, but not limited to, surgical methods (e.g., surgical isolation of an effector structure from sympathetic and/or parasympathetic innervation, i.e., surgically isolating an effector structure from one or more sympathetic and/or parasympathetic nerve fibers associated with it); ablation (permanently or reversibly ablating a nerve by employing energy delivery devices or cryotherapy); cryoablation; thermoablation; microwave energy; focus ultrasound; magnetic fields including internal and external magnetic fields; laser energy; optical energy; radiofrequency energy; pacing mechanisms (e.g., implantable electrode-based pacing systems, external magnetic-based pacing system, and the like); transcutaneous electrical nerve stimulation ("TENS") or transmagnetic stimulation ("TMS") (see for example George, M. Stimulating the Brain. Sci Amer 2003 September); pharmacological modulation and electrical modulation. Accordingly, as will be described in greater detail below, certain embodiments may include employing an electric energy supplying device to modulate at least a portion of the autonomic nervous system wherein the device may incorporate an immunomodulator such as a steroid or the like on a subject's contacting surface. Such a device may be permanently or temporarily implanted.

Modulation of the autonomic nervous system may also be accomplished at least in part by modulating receptors, e.g., beta adrenergic receptors, immunomodulatory receptors, and the like, or various enzymes associated with renal dysfunction. Accordingly, increasing the parasympathetic activity/sympathetic activity ratio may be accomplished by modulating receptors, e.g., to stimulate or inhibit signal transduction and/or increase or decrease binding affinity. For instance, the methods of the subject invention may include targeting a receptor to modulate it in a manner to increase parasympathetic activity/sympathetic activity ratio in at least a portion of the autonomic nervous system to treat a subject for a renal associated condition. The activity of a receptor may be increased or decreased (e.g., a receptor may be blocked), depending on the type of receptor so as to achieve desired result e.g., to increase parasympathetic activity/sympathetic activity ratio. For example, the particulars as to receptor modulation may depend on, e.g., whether it is desirable to increase ligand binding affinity to the receptor, decrease ligand binding affinity, increase signal transmission, decrease signal transmission, etc. Receptors that may be targeted include sympathetic receptors and parasympathetic receptors.

For example, pro-sympathetic receptors, the activation of which may promote renal stress, and which may be targeted to treat a subject for a renal condition, but are not limited to the following receptors: catecholamine, noradrenaline, interferon alpha, interferon beta, interferon gamma, CD 20, CD 3, Interleukin 1-13 and 18, estrogen, testosterone, gonadotropin releasing hormone, oxytocin, alcohol, adrenaline, dehydroepiandrostonedione, glucagons-like peptide 1, leptin, and histamine, etc. Other receptors that may be targeted include prothrombin receptors, thrombin receptors, fibrinogen receptors; beta receptors, alpha receptors, aldosterone receptors, anti-diuretic hormone receptors, angiotensin I receptors, angiotensin II receptors, renal distal tubule transporters, loop of henle transporters, renal proximal tubule transporters, cholinergic receptors, sodium channels, calcium channels, relaxin, nicotoine receptors, muscarinic receptors, phosphodiesterase receptors, cholinergic receptors, magnesium channels, progesterone receptors, etc.

Embodiments may also include modulating (e.g., activating or de-activating) one or more enzymes in a manner to increase parasympathetic activity/sympathetic activity ratio in at least a portion of the autonomic nervous system to treat a subject for a renal associated condition. For example, pro sympathetic enzymes that may be modulated to treat a subject include, but are not limited to the following enzymes: HMG CoA reductase, acetylcholinesterase, vesicular monoamine transporter, dipeptidyl peptidase IV, Factor Va, Factor VII, Factor VIIa, Factor VIIIa, Factor IX, Factor IXa, Factor X, Factor Xa, Factor XI, Factor XIa, Factor XII, Factor XIIa, Factor XIIIa, angiotensin converting enzyme, rennin, nitric oxide, phosphodiesterase, etc.

As will be described in greater detail below, certain embodiments of the subject invention may include treating a subject for a renal associated condition by pharmacologically modulating at least a portion of the subject's autonomic nervous system. By "pharmacologically modulating at least a portion of a subject's autonomic nervous system" is meant altering or changing at least a portion of an autonomic nervous system by pharmacological means to provide a change, alteration or shift in at least one component or aspect of the autonomic nervous system. Exemplary pharmacological agents that may be employed to modulate a portion of a subject's autonomic nervous system to treat the subject for renal associated condition include, but are not limited to, those described herein and elsewhere.

In certain embodiments, to accomplish the modulation of at least a portion of a subject's autonomic nervous system electrical energy (electrical modulation) may be applied to at least a portion of a subject's autonomic nervous system, where such electrical energy may be excitatory or inhibitory and in certain embodiments may include both excitatory and inhibitory stimulation. Embodiments of the subject methods may also, in addition to electrical energy, include administering at least one pharmacological agent (pharmacological modulation) to said subject to modulate at least a portion of a subject's autonomic nervous system.

Increasing Activity in at Least a Portion of the Autonomic Nervous System

As noted above, in certain embodiments activity in at least a portion of the autonomic nervous system is increased. For example, any portion of the parasympathetic system, e.g., one or more nerve fibers, may be pharmacologically and/or electrically stimulated to increase parasympathetic activity to provide the desired ratio of parasympathetic/sympathetic activity. In other words, activity in at least a portion of the parasympathetic nervous system may be increased pharmacologically and/or electrically such that at least a portion of the parasympathetic nervous system may be "up-regulated". Likewise, any portion of the sympathetic system, e.g., one or more nerve fibers, may be pharmacologically and/or electrically stimulated to provide the desired ratio of parasympathetic/sympathetic activity. In other words, activity in at least a portion of the sympathetic nervous system may be increased pharmacologically and/or electrically such that at least a portion of the sympathetic nervous system may be "up-regulated".

In certain embodiments, increasing activity in, or up-regulating, at least a part of the parasympathetic system may be desired in instances where, prior to the application of autonomic nervous system-modulating electrical energy and/or the administration of an effective amount of at least one pharmacological agent, sympathetic activity is higher than desired, e.g., higher than parasympathetic activity (e.g., there exists a relative sympathetic bias) and as such the subject methods may be employed to increase parasympathetic activity to a level above or rather to a level that is greater than sympathetic activity or may be employed to modulate the differential between the parasympathetic-sympathetic systems such that the result of increasing parasympathetic activity may be a sympathetic bias, parasympathetic bias or may be an equalization of the two systems (i.e., the activities of the two systems are approximately equal—including equal), but the difference between the parasympathetic-sympathetic systems may be modulated, e.g., reduced or minimized or increased in certain embodiments. Accordingly, the subject methods may be employed to increase parasympathetic activity above that of sympathetic activity and/or may be employed to modulate (increase or decrease) the differential between the two systems, but in certain embodiments may be employed to increase the parasympathetic activity/sympathetic activity ratio.

In certain embodiments, a sympathetic bias may be the normal state, but the ratio of the two systems may be abnormal or otherwise contributing to a condition. Increasing parasympathetic bias may also be desired in instances where, prior to the application of autonomic nervous system-modulating the administration of an effective amount of at least one pharmacological agent and/or electrical energy, parasympathetic activity is higher than the sympathetic activity, but the differential between the two needs to be modulated such as increased further, e.g., the sympathetic activity is normal or above normal (i.e., abnormally high) and/or the parasympathetic activity is normal or below normal (i.e., abnormally low) or above normal (i.e., abnormally high).

For example, such instances may occur where a subject has normal or above normal parasympathetic function, but also has elevated sympathetic function. Other instances may include below normal parasympathetic function, but normal or elevated sympathetic function, etc. It may also be desirable to increase parasympathetic function in instances where the respective activities of the two system are analogous or approximately equal, including equal, prior to increasing activity in the parasympathetic system, but the level of one or both is abnormally high or abnormally low. The above-described examples of instances where increasing parasympathetic activity may be desired is exemplary only and is in no way intended to limit the scope of the invention and other instances where increasing parasympathetic activity may be desired will be apparent to those of skill in the art.

While the subject methods are described primarily with respect to increasing activity in the parasympathetic system, it is to be understood that this is for exemplary purposes only and is in no way intended to limit the scope of the invention as activity may also, or in addition, be increased in at least a portion of the sympathetic nervous system.

Inhibiting Activity in at Least a Portion of the Autonomic Nervous System

As noted above, in certain embodiments activity in at least a portion of the sympathetic system may be inhibited to modulate at least a portion of the autonomic nervous system. For example, activity in any portion of the sympathetic nervous system may be inhibited, e.g., to provide the desired ratio of parasympathetic/sympathetic activity, e.g., activity in one or more sympathetic nerve fibers may be inhibited. Likewise, activity in at least a portion of the parasympathetic system may be inhibited to modulate at least a portion of the autonomic nervous system. For example, activity in any portion of the parasympathetic nervous system may be inhibited, e.g., to provide the desired ratio of parasympathetic/sympathetic activity, e.g., activity in one or more parasympathetic nerve fibers may be inhibited. By "inhibited" is meant to include disruption, down-regulating, dampening and partial and complete blockage of nerve impulses in a particular area of the autonomic nervous system.

Inhibiting or "down-regulating" activity in at least a part of the autonomic nervous system, e.g., in at least a portion of the sympathetic system, may be desired in instances where, prior to the inhibition of activity in, e.g., at least one sympathetic nerve fiber, the sympathetic activity is higher than desired. For example, sympathetic activity may be higher than the parasympathetic activity (i.e., there exists a sympathetic bias) or sympathetic activity may be less than or approximately equal to, including equal, to parasympathetic activity, and the subject methods may be employed to modulate the differential between the parasympathetic-sympathetic systems such that the result of decreasing sympathetic activity may be a sympathetic bias, parasympathetic bias or may be an equalization of the two systems (i.e., the activities of the two systems are approximately equal—including equal), but the difference between the parasympathetic-sympathetic systems may be modulated, e.g., increased or reduced in certain embodiments. Accordingly, the subject-methods may be employed to decrease sympathetic activity below that of sympathetic activity and/or may be employed to modulate (decrease or increase) the differential between the two systems, where in certain embodiments may be employed to increase the ratio of parasympathetic activity to sympathetic activity.

For example, decreasing activity in at least a portion of the sympathetic system may be employed where there is a normal or an abnormally low parasympathetic function and/or abnormally high sympathetic function. Such may also be desired in instances where, prior to decreasing sympathetic function in, e.g., at least one sympathetic nerve fiber, parasympathetic activity is higher than the sympathetic activity, but the differential between the two needs to be increased further. For example, such instances may occur where a subject has normal or above normal (i.e., abnormally high) parasympathetic function, but also has elevated sympathetic function (i.e., abnormally high), e.g., a relative bias towards sympathetic function may be present. Other instances include normal or below normal (i.e., abnormally low) parasympathetic activity and/or normal or above normal (i.e., abnormally high) sympathetic activity. The above-described examples of instances where decreasing sympathetic activity may be desired is exemplary only and is in no way intended to limit the scope of the invention and other instances where decreasing sympathetic activity to provide an increase in the parasympathetic activity/sympathetic activity ratio may be desired will be apparent to those of skill in the art.

Inhibiting or down-regulating at least a portion of the autonomic nervous system may be accomplished in a number of ways. For example, inhibition or down-regulation of activity may be achieved by surgically isolating an effector structure (i.e., the target of the sympathetic activity) from sympathetic innervation, i.e., surgically isolating an effector structure from one or more sympathetic nerve fibers associated with it. Furthermore, sympathetic nerves may be ablated, permanently or reversibly, by employing energy delivery devices or cryotherapy. Certain embodiments may employ cryoablation, thermoablation, microwave energy, focus ultrasound, magnetic fields including internal and external magnetic fields, laser energy, optical energy, radiofrequency energy, and the like. The sympathetic system may also be inhibited or down-regulated or depressed by employing one or more pharmacological agents to disable sympathetic and/or paraympathetic function, e.g., such that the parasympathetic to sympathetic ratio is increased temporarily or permanently. Still further, the sympathetic system may also be inhibited or down-regulated or depressed by employing pacing mechanisms such as implantable electrode-based pacing systems, external magnetic-based pacing system, and the like. Certain embodiments may include inhibiting activity in at least a portion of the sympathetic nervous system using transcutaneous electrical nerve stimulation ("TENS") or transmagnetic stimulation ("TMS") (see for example George, M. Stimulating the Brain. Sci Amer 2003 September).

As the subject methods include modulating at least a portion of a subject's autonomic nervous system, the modulation may be systemic or regional (i.e., localized). In other words, the entire autonomic nervous system may be modulated (e.g., the entire sympathetic nervous system and/or parasympathetic nervous system may be modulated) or only a portion of the autonomic nervous system may be modulated (e.g., only a portion of the sympathetic nervous system and/or parasympathetic nervous system may be modulated). Localization may be with respect to a particular area, organ or even to a particular nerve fiber. For example, localization may be with respect to innervations of one or more organs.

While the subject methods are described primarily with respect to decreasing activity in the sympathetic system, it is to be understood that this is for exemplary purposes only and is in no way intended to limit the scope of the invention as activity may also, or in addition, be decreased in at least a portion of the parasympathetic nervous system.

Increasing Activity in at Least a Portion of the Autonomic Nervous System and Inhibiting Activity in at Least a Portion of the Autonomic Nervous System As noted above, in certain embodiments activity in at least a portion of the autonomic nervous system may be increased and activity in at least a portion of the autonomic nervous system may be decreased. For example, in certain embodiments activity in at least a portion of the parasympathetic system may be increased and activity in at least a portion of the sympathetic system may be inhibited, e.g., to increase the parasympathetic activity/sympathetic activity ratio. As described above, any portion of the parasympathetic and/or sympathetic nervous systems may be electrically and/or pharmacologically modulated to increase activity and activity in any portion of the sympathetic and/or parasympathetic nervous system may be inhibited to provide the desired ratio of parasympathetic activity to sympathetic activity. Such a protocol may be employed, e.g., in instances where parasympathetic function is normal or abnormally low and/or sympathetic function is normal or abnormally high where normal is determined by the typical or average autonomic nervous system functions for a healthy subject, e.g., a healthy human subject ranging in age from about 20 years old to about 25 years old.

Embodiments wherein activity in at least a portion of the autonomic nervous system may be increased and activity in at least a portion of the autonomic nervous system may be decreased may be employed to alter the dominance and/or may be employed to modulate the differential between the two systems. For example, prior to modulating the autonomic system according to the subject invention, the activity in the sympathetic system may be higher than activity in the parasympathetic system and the subject methods may be employed to increase the parasympathetic activity to a level that is greater than the sympathetic activity and/or may be employed to alter the differential or difference in activity levels of the two systems such as decreasing the difference in activity levels or increasing the difference in activity levels. In other embodiments, prior to modulating the autonomic system according to the subject invention, the activity in the parasympathetic system may be higher than activity in the sympathetic system and the subject methods may be employed to alter the differential or difference in activity levels of the two systems such as increasing the difference in activity levels. The above-described examples of instances where increasing activity in at least a portion of the parasympathetic system and decreasing activity in at least a portion of the sympathetic activity may be desired is exemplary only and is in no way intended to limit the scope of the invention and other instances where increasing activity in at least a portion of the parasympathetic system and decreasing activity in at least a portion of the sympathetic activity may be desired will be apparent to those of skill in the art.

Increasing activity in at least a portion of the autonomic nervous system, e.g., increasing activity in at least a portion of the parasympathetic system, and decreasing activity in at least a portion of the autonomic nervous system, e.g., decreasing activity in at least a portion of the sympathetic system, may be performed simultaneously or sequentially such that at least a portion of the autonomic nervous system, e.g., at least a portion of the parasympathetic nervous system, may be pharmacologically and/or electrically modulated to increase activity therein prior or subsequent to inhibiting activity in at least a portion of the autonomic nervous system e.g., at least a portion of the sympathetic nervous system, such as by electrical and/or pharmacological means.

Regardless of whether increasing activity in at least a portion of the autonomic nervous system, e.g., in at least a portion of the parasympathetic system, and decreasing activity in at least a portion of the autonomic nervous system, e.g., in at least a portion of the sympathetic system, is performed simultaneously or sequentially, the parameters for increasing activity in at least a portion of autonomic nervous system and decreasing activity in at least a portion of the autonomic nervous system may be analogous to that described above.

As noted above, modulation of at least a portion of the autonomic nervous system to treat a condition may be accomplished in any suitable manner, where pharmacological and electrical modulation are two exemplary methods that may be employed in the practice of the subject methods. Each of these are now described in greater detail.

Pharmacological Agents

In certain embodiments, the subject invention includes administering an effective amount of a pharmacological agent to a subject. In certain embodiments, as will be described in further detail below, the pharmacological agent to be administered is an autonomic nervous system modulator that is administered in a therapeutically effective amount. That is, embodiments of the subject methods include administering an effective amount, i.e., a therapeutically effective amount, of one or more autonomic nervous system modulators to a subject.

By "effective amount" is meant a dosage sufficient to prevent or treat a renal associated condition, such as but not limited to cardio renal failure, in a subject as desired. The effective amount will vary somewhat from subject to subject, and may depend upon factors such as the age and physical condition of the subject, severity of the renal condition being treated, the duration of the treatment, the nature of any concurrent treatment, the form of the agent, the pharmaceutically acceptable carrier used if any, the route and method of delivery, and analogous factors within the knowledge and expertise of those skilled in the art. Appropriate dosages may be determined in accordance with routine pharmacological procedures known to those skilled in the art, as described in greater detail below.

If a pharmacological approach is employed in the treatment of a given disease, the specific nature and dosing schedule of the agent will vary depending on the particular nature of the disease to be treated. Representative pharmacological agents that may find use in certain embodiments of the subject invention include both pro parasympathetic and pro sympathetic agents.

Pro parasympathetic agents of interest include, but are not limited to: Beta Blockers, e.g., atenolol (Tenormin R), betaxolol (Kerlone R), bisoprolol (Zebeta R), carvedilol (Coreg R), esmolol (Brevibloc R), labetalol (Normodyne R), metoprolol (Lopressor R), nadolol (Corgard R), pindolol (Visken R), propranolol (Inderal R), sotalol (Betapace R), timolol (Blocadren R); Aldosterone Antagonists, e.g., Spironolactone, eplerenone, Angiotensin II Receptor Blockade, candesartan (Atacand R), irbesartan (Avapro R), losartan (Cozaar R), telmisartan (Micardis R) valsartan (Diovan R), eprosartan mesylate (Teveten); ACE inhibitors, e.g., Benazepril (Lotensin R), Captopril (Capoten R), Enalapril (Vasotec R), Fosinopril (Monopril R), Lisinopril (Prinivil R), Moexipril (Univasc R), Quinapril (Accupril R), Ramipril (Altace R), Trandolapril (Mavik R); Statins, e.g., atorvastatin (Lipitor R), cerivastatin (Baycol R), fluvastatin (Lescol R), lovastatin (Mevacor R), pravastatin (Pravachol R), mvastatin (Zocor R); Triglyceride Lowering Agents, e.g., fenofibrate (Tricor R), gemfibrozil (Lopid R), Niacin; Diabetes Agents, e.g., acarbose (Precose R), glimepiride (Amaryl R), glyburide (Micronase R, Diabeta R), metformin (Glucophage R), Miglitol (Glycet R), pioglitazone (Actos R), repaglinide (Prandin R), rosiglitazone (Avandia R); Immunomodulators, e.g., Interferon Alfa-2A (Roferon-A), Interferon Alfa-2b (Intron-A), Interferon Alfa-2b and Ribavirin combo Pack (Rebetron), Interferon Alfa-N3 (Alferon N), Interferon Beta-1A (Avonex), Interferon Beta-1B (Betaseron), Interferon Gamma; agents thatbinds/reacts to CD4, gp39, B7, CD19, CD20, CD22, CD401, CD40, CD40L and CD23 antigens, rituximab, Nicotine; Sympathomimetics, e.g., trimethaphan, Clonidine, Reserpine, Guanethidine; Antihistamines, e.g., Benadryl, Diphenhydramine, Actifed (Triprolidine), PBZ (Tripelenamine), Allegra (Fexofenadine), Periactin (Cyproheptadine), Antivert or Bonine (Meclizine), Phenergan (Promethazine), Astelin (dispensed as a Nose Spray), Polyhistine (Phenyltoloxamine), Atarax (Hydroxyzine), Seldane (Terfenadine), Benadryl (Diphenhydramine), Semprex (Acrivastine), Bromfed (Bromphener-amine), Tavist (Clemastine), Chlortrimeton (Chlorpheniramine), unisom (Doxylamine), Claritin (Loratidine), Zyrtec (Cetirizine), Dramamine (Dimenhydrinate); Cholinergics, e.g., Bethanechol, Oxotremorine, Methacholine, Cevimeline, Carbachol, Galantamine, Arecoline, Levaminsole; Acetylcholinesteriase Inhibitors, e.g., Edrophonium, Neostigmine, Donepezil, Tacrine, Echothiophate, Diisopropylfluorophosphate, Demecarium, Pralidoxime, Galanthamine, Tetraethyl pyrophosphate, Parathoin, Malathion, Isoflurophate, Metrifonate, Physostigmine, Rivastigmine, Abenonium, acetylchol, Carbaryl acetylchol, Propoxur acetylchol, Aldicarb acetylchol, Muscarinics, Muscarine, Pilocarpine, Magnesium; Calcium channel blockers, e.g., amlodipine besylate, Norvasc, diltiazem hydrochloride Cardizem CD, Cardizem SR, Dilacor XR, Tiazac, felodipine Plendil, isradipine DynaCirc, DynaCirc CR, nicardipine Cardene SR, nifedipine Adalat CC, Procardia XL, nisoldipine Sular, verapamil hydrochloride Calan SR, Covera HS, Isoptin SR, Verelan; Sodium channel blockers, e.g., moricizine, propafenone, encainide, flecainide, Tocainide, mexiletine, Phenyloin, Lidocaine, Disopyramide, Quinidine, Procainamide; Glucocorticoid receptor blocker, e.g., (Mifepristone); Peripheral adrenergic inhibitors, e.g., guanadrel Hylorel, guanethidine, monosulfate Ismelin, reserpine Serpasil, Mecamylamine, Hexemethonium; Blood vessel dilators, e.g., hydralazine hydrocholoride Apresoline, minoxidil Loniten; Central agonists, e.g., alpha methyldopa Aldomet, clonidine hydrochloride Catapres, guanabenz, acetate Wytensin, guanfacine hydrochloride Tenex; Combined alpha and beta blockers, e.g., labetolol hydrochloride, Normodyne, Trandate, carvedilol Coreg; Alpha blockers, e.g., doxazosin mesylate Cardura, prazosin hydrochloride Minipress, terazosin, hydrochloride Hytrin; Combination diuretics, e.g., amiloride hydrochloride+hydrochlorothiazide Moduretic, spironolactone+hydrochlorothiazide Aldactazide, triamterene+hydrochlorothiazide Dyazide, Maxzide; Potassium-sparing diuretics, e.g., amiloride hydrochloride Midamar, spironolactone Aldactone, triamterene Dyrenium; Nitrate pathway modulators, e.g., L-arginine, Nitroglycerin Deponit, Minitran, Nitropar, Nitrocine, Nitro Disc, Nitro-Dur, Nitrogard, Nitroglycerin, Nitroglycerin T/R, Nitro-Time, Nitrol ointment, Nitrolingual Spray, Nitrong, Nitro-Bid, Nitropress, Nitroprex, Nitro S.A, Nitrospan, Nitrostat, Nitro-Trans System, Nitro-Transdermal, Nitro-Time, Transderm-Nitro, Tridil. Pentaerythrito, I Tetranitrate, Peritrate, Peritrate S.A, Erythrityl, Tetranitrate, Cardilate, Isosorbide Dinitrate/Phenobarbital Isordil w/PB Isosorbide, Mononitrate, Imdur, ISMO, Isosorbide, Mononitrate, Monoket, Isosorbide, Nitrate; Cyclic nucleotide monophosphodiesterase (PDE) inhibitors; e.g., Levitra (vardenafil), Cialis (tadalafil), Viagra (sildenafil); Vasopressin inhibitors, e.g., atosiban, Alcohol, Relaxin; Renin inhibitors; e.g., Aliskiren; Estrogen and estrogen analogues and estrogen metabolites; Vesicular monoamine transport (VMAT) inhibitors; e.g., reserpine, tetrabenazine, Melatonin, Melatonin Analogues, 6-chloromelatonin, 2,3, dihydromelatonin, 6-chloro-2,3-dihydromelatonin, N-acetyl-N2-formyl-5-methoxy, kynurenamine, N-acetyl-5-methoxy kynurenamine; Progestrone inhibitors, e.g, ru486; Testosterone inhibitors, e.g., Spironolactone, cyproterone acetate; Gonadotropin-releasing hormone inhibitors, e.g., Leuprolide Acetate; Oxytocin inhibitors, e.g., Terbutaline Ritodrine, Glucagon Like Peptide 1; Dipeptidyl Peptidase IV inhibitors, e.g., LAF237 (novartis), P93/01 and P32/98 (Probiodrug AB), valine pyrrolidide (Novo Nordisk), dhea, adiponectin, phenserine, phosphodiesterase 4 inhibitor, valproate; Anticoagulants, e.g., Exanta (ximelagatran)-, Bilivarudin (hirulog), abciximab (Reopro®), Aggrenox® (dipridamole/ASA), anagrelide (Agrylin®), clopidogrel (Plavix), dipyridamole (Persantine®), tifabatide (Integrelin), ticlopidine (Ticlid®), tirofiban (aggrastat), ardeparin (Normiflo), Dalteparin (Fragmin), Danaparoid (Organan), Enoxaparin (lovenox), lepirudin (Refludan), Heparin, Warfarin; Thrombolytics, e.g., alteplase (Activase®, t-PA), reteplase (Retevase), Streptokinase, Urokinase; Other anticoagulants, e.g., aminocaproic acid (Amicar®), cilostazol (Pletal), erythropoietin (Epogen), filgrastim (G-CSF, Neupogen®), oprelvekin (Neumega), pentoxifylline (Trental); hmg1 antagonist; botox; and the like.

Pro sympathetic agents of interest include, but are not limited to: Beta-agonists, e.g., dobutamine, terbutaline, ritodrine, albuterol, metaproterenol; Alpha-1 agonists, e.g., phenylephrine, metaraminol, methoxamine; Prednisone & steroids; Indirect agents that include, but are not limited to, NE, ephedrine, phenylpropanolamine, cyclopentamine, tuaminoheptane, naphazoline, ampthetamine, tetrahydrozoline; Epinephrine/norepinephrine, Acetylcholine, Sodium, Calcium, ACE, Angiotensin, Aldosterone, Aldosterone Analogues, Fludrocortisone, 18-oxocortisol, deoxycorticosterone pivalate (DOCP) (ciba-geigy animal health); Potassium or magnesium channel blockers, e.g., valproate lithium, Cocaine; Amphetamines, e.g., Ephedrine, Terbutaline, Dopamine, Bromocriptine (Parlodel), Levodopa/Carbidopa, Dobutamine; Acupunture; Adh vasopressin; Oxytocin pitocin; THC cannabinoids; Progesterone; Leptin; Galanin like peptide Accordingly, a variety of suitable pharmacological autonomic nervous system modulator may be administered. In certain embodiments, the autonomic nervous system modulator is an anti-adrenergic agent. In certain embodiments, the anti-adrenergic agent is administered so as to increase parasympathetic activity. In other embodiments, the anti-adrenergic agent is administered so as to decrease sympathetic activity. In further embodiments, one or more anti-adrenergic agents are administered so as to both increase parasympathetic activity and decrease sympathetic activity.

Suitable anti-adrenergic agents include, but are not limited to: beta-blockers; aldosterone antagonists; angiotensin II receptor blockades; angiotensin converting enzyme ("ACE") inhibitors; sympathomimetics; calcium channel blockers; sodium channel blockers; vasopressin inhibitors; peripheral adrenergic inhibitors; oxytocin inhibitors, and botulism toxin; statins; triglycerides lowering agents; niacin; diabetes agents; immunomodulators; nicotine; sympathomimetics; antihistamines; cholinergics; acetylcholinesterase inhibitors; magnesium and magnesium sulfates; calcium channel blockers; muscarinics; sodium channel blockers; glucocorticoid receptor blockers; blood vessel dilators; central agonists; combined alpha and beta-blockers; alpha blockers; combination diuretics; potassium sparing diuretics; cyclic nucleotide-monophosphodiesterase inhibitors; alcohols; vasopressin inhibitors; oxytocin inhibitors; glucagons like peptide 1; relaxin hormone; renin inhibitors; estrogen and estrogen analogues and metabolites; progesterone inhibitors; testosterone inhibitors; gonadotropin-releasing hormone analogues; gonadotropin-releasing hormone inhibitors; type 4 phosphodiesterase inhibitors; vesicular monoamine transport inhibitors; melatonin; anticoagulants; beta agonists; alpha agonists; indirect agents that include norepinephrine; epinephrine; norepinephrine; acetylcholine; sodium; calcium; angiotensin I; angiotensin II; angiotensin converting enzyme I; angiotensin converting enzyme II; aldosterone; potassium channel blockers and magnesium channel blockers; cocaine; amphetamines; ephedrine; terbutaline; dopamine; doputamine; antidiuretic hormone; oxytocin; and THC cannabinoids.

Specific anti-adrenergic autonomic nervous system modulators that may be employed in the practice of the subject invention, include, but are not limited to one or more of: beta-blockers: atenolol (e.g., as sold under the brand names Tenormin), betaxolol (e.g., as sold under the brand name Kerlone), bisoprolol (e.g., as sold under the brand name Zebeta), carvedilol (e.g., as sold under the brand name Coreg), esmolol (e.g., as sold under the brand name Brevibloc), labetalol (e.g., as sold under the brand name Normodyne), metoprolol (e.g., as sold under the brand name Lopressor), nadolol (e.g., as sold under the brand name Corgard), pindolol (e.g., as sold under the brand name Visken), propranolol (e.g., as sold under the brand name Inderal), sotalol (e.g., as sold under the brand name Betapace), timolol (e.g., as sold under the brand name Blocadren), carvedilol, and the like; aldosterone antagonists: e.g., spironolactone, eplerenone, and the like; angiotensin II receptor blockades: e.g., candeartan (e.g., available under the brand name Altacand), eprosarten mesylate (e.g., available under the brand name Tevetan), irbesartan (e.g., available under the brand name Avapro), losartan (e.g., available under the brand name Cozaar), etelmisartin (e.g., available under the brand name Micardis), valsartan (e.g., available under the brand name Diovan), and the like; angiotensin converting enzyme ("ACE") inhibitors: e.g., benazapril (e.g., available under the brand name Lotensin), captopril (e.g., available under the brand name Capoten), enalapril (e.g., available under the brand name Vasotec), fosinopril (e.g., available under the brand name Monopril), lisinopril (e.g., available under the brand name Prinivil), moexipril (e.g., available under the brand name Univasc), quinapril (e.g., available under the brand name AccupriL), ramipril (e.g., available under the brand name Altace), trandolapril (e.g., available under the brand name Mavik), and the like; sympathomimetics: e.g., trimethaphan, clondine, reserpine, guanethidine, and the like; calcium channel blockers: e.g., amlodipine besylate (e.g., available under the brand name Norvasc), diltiazem hydrochloride (e.g., available under the brand names Cardizem CD, Cardizem SR, Dilacor XR, Tiazac), felodipine isradipine (e.g., available under the brand names DynaCirc, DynaCirc CR), nicardipine (e.g., available under the brand name Cardene SR), nifedipine (e.g., available under the brand names Adalat CC, Procardia XL), nisoldipine sulfur (e.g., available under the brand name Sular), verapamil hydrochloride (e.g., available under the brand names Calan SR, Covera HS, Isoptin SR, Verelan) and the like; sodium channel blockers: e.g., moricizine, propafenone, encainide, flecainide, tocainide, mexiletine, phenyloin, lidocaine, disopyramide, quinidine, procainamide, and the like; vasopressin inhibitors: e.g., atosiban (Tractocile), AVP Via (OPC-21268, SR49059 (Relcovaptan)), V2 (OPC-31260, OPC-41061 (Tolvaptan), VPA-985 (Lixivaptan), SR121463, VP-343, FR-161282) and mixed V1a/V2 (YM-087 (Conivaptan), JTV-605, CL-385004) receptor antagonists, and the like; peripheral adrenergic inhibitors: e.g., guanadrel (e.g., available under the brand name Hylorel), guanethidine monosulfate (e.g., available under the brand name Ismelin), reserpine (e.g., available under the brand names Serpasil, Mecamylamine, Hexemethonium), and the like; blood vessel dilators: e.g., hydralazine hydrocholoride (e.g., available under the brand name Apresoline), minoxidil (e.g., e.g., available under the brand name Loniten), and the like; central agonists: e.g., alpha methyldopa (e.g., available under the brand name Aldomet), clonidine hydrochloride (e.g., available under the brand name Catapres), guanabenz acetate (e.g., available under the brand name Wytensin), guanfacine hydrochloride (e.g., available under the brand name Tenex), and the like; combined alpha and beta-blockers: e.g., carvedilol (e.g., available under the brand name Coreg), labetolol hydrochloride (e.g., available under the brand names Normodyne, Trandate), and the like; alpha blockers: e.g., doxazosin mesylate (e.g., available under the brand name Cardura), prazosin hydrochloride (e.g., available under the brand name Minipress), terazosin hydrochloride (e.g., available under the brand name Hytrin), and the like; renin inhibitors: e.g., Aliskiren, and the like; oxytocin inhibitors: e.g., terbutaline, ritodrine, and the like, and botulism toxin (or botox) and the like.

Other suitable pharmacological agents include, but are not limited to: adiponectins; phenserines; phosphodiesterase 4 inhibitors; valproate; glucagon; glucagon-like peptide-1; glucocorticoid receptor blockers; nicotine; potassium channel blockers; combination diuretics; potassium sparing diuretics; nitrate compounds; gonadotropin-releasing hormone analogues; vesicular monoamine transport (VMAT) inhibitors; statins; cyclic nucleotide monophosphodiesterase (PDE) inhibitors; alcohols; relaxin; estrogen; estrogen analogues; estrogen metabolites; melatonin; triglyceride lowering agents; niacin; anti-diabetic agents; cholinergics; acetylcholinesteriase inhibitors; muscarinics; magnesium; dipeptidyl peptidase IV inhibitors; dhea; hmg1 antagonists; leptin; Galanin like peptide; gonadotropin-releasing hormone inhibitors; testosterone inhibitors; and progestrone inhibitors.

In certain embodiments, as will be described in greater detail below, more than one type of agent may be administered at the same or different times to treat the renal condition. For instance, in certain embodiments the subject methods include administering an agent so as to modulate a receptor, an enzyme, or both so as to increase the parasympathetic activity/sympathetic activity ratio in at least a portion of said subject's autonomic nervous system in a manner effective to treat said renal associated dysfunction in the subject. In one embodiment, the receptor or enzyme or both to be modulated is a sympathetic receptor or enzyme and the method involves decreasing the activity of the receptor or the enzyme or both so as to decrease sympathetic activity. In another embodiment, the receptor or enzyme or both to be modulated is a parasympathetic receptor or enzyme and the method involves increasing the activity of the receptor or enzyme or both so as to increase parasympathetic activity.

Additional agents of interest that may be used in a given situation are disclosed in U.S. patent application Ser. Nos. 10/661,368; 10/748,897; 10/748,976; 10/871,366; 10/846,486 10/917,270; 10/962,190 11/060,643 11/251,629; 11/238,108; 60/654,139 and 60/702,776; the disclosures of which are herein incorporated by reference.

Formulations of Pharmacological Agents

Pharmacological agents for administration to a subject may be incorporated into any suitable formulation along with a pharmaceutically acceptable carrier. The pharmacological agents employed in the subject methods may be formulated into preparations in solid, semi-solid (e.g., gel), liquid or gaseous forms, such as tablets, capsules, powders, granules, ointments, solutions, injections, inhalants, aerosols, and suppositories. Accordingly, a pharmacological agent may be formulated into pharmaceutical compositions in suitable dosage form by combination with appropriate pharmaceutically acceptable carriers.

By "pharmaceutically acceptable carrier" is meant a component such as a carrier, diluent, excipient, and the like of a composition that is compatible with the one or more pharmacological agents and other optional ingredients of the subject pharmacological agent compositions in that a pharmaceutically acceptable carrier may be combined with the pharmacological agent(s) without eliminating the biological or therapeutically effective activity of the one or more pharmacological agents, and is suitable for use in subjects as provided herein without undue adverse side effects (such as toxicity, irritation, allergic response, and death). Side effects are "undue" when their risk outweighs the benefit provided by the pharmaceutical agent. Pharmaceutically acceptable carriers enable the pharmaceutical agents to be formulated in unit dosage forms as tablets, pills, powder, dragees, capsules, liquids, lozenges, gels, syrups, slurries, suspensions, etc., suitable for ingestion by the patient.

In certain embodiments, the pharmacological agent formulations may be prepared by uniformly and intimately admixing the active pharmacological agent(s) with a finely divided solid carrier, or a liquid, or both, and then, if necessary, shaping the resulting mixture. For example, pharmaceutical preparations for oral use may be formulated as a tablet. The pharmacological agent may be prepared and formulated in combination with one or more solid excipients by grinding the pharmacological agent with the excepient, and any other suitable additional compounds desired, such as a binder, lubricant, inert diluent, and/or surface active/dispersing agent(s), so as to generate a free flowing mixture, and compressing or molding the powder or granules containing the active pharmacological agent and the optional one or more accessory ingredients into the desired shape. Molded tablets may be made by molding, in a suitable machine, the powdered pharmacological agent moistened with an inert liquid binder. Additionally, the pharmacological agent formulations for use with the subject invention may be prepared by uniformly and intimately admixing the active pharmacological agent(s) with phosphate buffered saline solutions, water, emulsions such as oil/water emulsions or water/oil emulsions, microemulsions, and various types of wetting agents, as is well known in the art.

Suitable solid excipients include, but are not limited to, carbohydrate or protein fillers and include, but are not limited to sugars, including lactose, sucrose, mannitol, or sorbitol; starch from corn, wheat, rice, potato, or other plants; cellulose such as methyl cellulose, hydroxypropyl-methyl-cellulose or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate; with optional lubricants, such as talc or magnesium stearate; and if desired, with diluents, buffering agents, moistening agents, preservatives and flavoring agents.

Pharmacological agents may be provided as a salt and may be formed with one or more acids, including but not limited to hydrochloric, sulfuric, acetic, lactic, tartaric, malic, succinic, etc. Salts tend to be more soluble in aqueous or other protonic solvents that are the corresponding free base forms. Accordingly, formulations of pharmacological agents may include compositions that are prepared from water-insoluble compounds, or salts thereof, such as aqueous base emulsions. In such embodiments, the pharmacological agent composition will typically contain a sufficient amount of a pharmaceutically acceptable emulsifying agent to emulsify the desired amount of the pharmacological agent. Useful emulsifying agents include, but are not limited to, phosphatidyl cholines, lecithin, and the like. In other cases, a preparation may be a lyophilized powder that is combined with buffer prior to use.

Additionally, the formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. Useful pH-adjusting agents include acids, such as hydrochloric acid, bases or buffers, such as sodium lactate, sodium acetate, sodium phosphate, sodium citrate, sodium borate, or sodium gluconate.

Furthermore, pharmacological agent compositions may, though not always, contain microbial preservatives. Microbial preservatives that may be employed include, but are not limited to, methylparaben, propylparaben, and benzyl alcohol. The microbial preservative may be employed when the pharmacological agent formulation is placed in a vial designed for multi-dose use.

In certain embodiments, a pharmaceutically acceptable carrier may be preservative free. By "preservative free" is meant the substantial absence of chemical, antibacterial, antimicrobial, or antioxidative additives, or the like, from the pharmaceutically acceptable carriers of the present invention. "Substantial absence" may mean that no preservative is present in the compositions or that trace amounts may be present that impart no detectable effect otherwise attributable to a preservative. For example, the pharmaceutically acceptable carrier may be characterized by the substantial absence of chemical, antibacterial, antimicrobial, or antioxidative additives or the like (e.g., contain less than about 5.0, 4.0, 3.0, 2.0, 1.0, 0.5, 0.1, 0.05, 0.01, or even about 0.00 percent by weight of a preservative). Further, such formulations may be substantially or essentially free of alcohols such as ethanol (e.g., contain less than about 5.0, 4.0, 3.0, 2.0, 1.0, 0.5, 0.1, 0.05, 0.01, or even about 0.00 percent by weight of alcohols such as ethanol).

Pharmaceutically acceptable excipients, such as vehicles, adjuvants, carriers or diluents, are well known and readily available to the public. Moreover, pharmaceutically acceptable auxiliary substances, such as pH adjusting and buffering agents, tonicity adjusting agents, stabilizers, wetting agents and the like, are also well known and readily available to the public. The concentration of pharmacological agent in these formulations may vary widely, and will be selected based on fluid volumes, viscosities, body weight, and the like, in accordance with the particular mode of administration selected and the patient's needs.

Accordingly, unit dosage forms for oral or rectal administration such as syrups, elixirs, and suspensions may be provided wherein each dosage unit, for example, teaspoonful, tablespoonful, tablet or suppository, contains a predetermined amount of a pharmacological agent. Similarly, unit dosage forms for injection or intravenous or other suitable administration route may include the pharmacological agent(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of pharmacological agent calculated in an amount sufficient to produce the desired effect in association with a pharmaceutically acceptable diluent, carrier or vehicle. The specifications for the unit dosage forms of pharmacological agents of the present invention depend on, for example, the particular pharmacological agent(s) employed and the effect to be achieved, the pharmacodynamics associated with the particular pharmacological agent(s) in the subject, etc.

A pharmaceutical composition of the subject invention in unit dosage form may optionally contain, in addition to a pharmacological agent for the treatment of a renal associated condition, at least one other therapeutic agent that is useful in the treatment of another condition, e.g., a condition associated with a renal condition, for instance a condition such as but not limited here to aging, atherosclerosis, renal artery stenosis, PMS, diabetes, contrast nephropathy, cancer, and/or post-operative hospitalization. In other words, a single agent administration entity may include two or more pharmacological agents. Such other compounds may be of any class of drug or pharmaceutical agent, including but not limited to antibiotics, anti-parasitic agents, antifungal agents, anti-viral agents, anti-tumor agents, anti-neurodegenerative agents and anti-psychotic agents. When administered with anti-parasitic, anti-bacterial, anti-fungal, anti-tumor, anti-viral agents, anti-neurodegenerative, and anti-psychotic agents and the like, pharmacological agents of the subject invention may be in any suitable formulation, as described above. For example, a single tablet, capsule, dragee, trocheem suppository, syringe, and the like, combining two or more pharmacological agents would be a unit dosage form.

As is known in the art the therapeutic agents present in a unit dosage form may be present in amounts such that, upon administration of one or more unit doses of the composition, a subject experiences, e.g., a longer lasting efficacy than with the administration of either agent alone and/or greater magnitude and/or quicker lowering of action. Such compositions may be included as part of a therapeutic package in which one or more unit doses are placed in a finished pharmaceutical container. Labeling may be included to provide directions for using the composition according to the invention.

The actual amounts of each agent in such single unit dosage forms may vary according to the specific compositions being utilized, the particular compositions formulated, the mode of application, the particular route of administration, and the like, where dosages for a given subject may be determined using conventional considerations, e.g., by customary comparison of the differential activities of the subject compositions and of a known agent, or by means of an appropriate, conventional pharmacological protocol. As described in more detail below, the pharmaceutical composition of the subject invention in unit dosage form may be administered by any method and route of administration suitable to the treatment of the condition, typically as pharmaceutical compositions.

Administration of Pharmacological Agents

The pharmacological agent(s) of the subject invention may be administered to a subject using any convenient means. As such, administration of a pharmacological agent may be achieved in various ways, including, but not limited to, oral, buccal (e.g. sub-lingual), parenteral (e.g., subcutaneous, intramuscular, intradermal, intravenous and intrathecal), intraperiactivityal, topical or transdermal (including both skin and mucosal surfaces, including airway surfaces), intracheal, intravaginal, endocervical, intrathecal, intranasal, intravesicular, in or on the eye, in the ear canal, rectal, vaginal, etc., administration. In certain embodiments, one or more pharmacological agents may be administered via a transdermal patch or film system such as or analogous to that described, e.g., in U.S. Pat. Nos. 6,503,532; 5,302,395; 5,262,165; 5,248,501; 5,232,702; 5,230,896; 5,227,169; 5,212,199; 5,202,125; 5,173,302; 5,154,922; 5,139,786; 5,122,383; 5,023,252; 4,978,532; 5,324,521; 5,306,503; 5,302,395; 5,296,230; 5,286,491; 5,252,334; 5,248,501; 5,230,896; 5,227,169; 5,212,199; 5,202,125; 5,173,302; 5,171,576; 5,139,786; 5,133,972; 5,122,383; 5,120,546; 5,118,509; 5,077,054; 5,066,494; 5,049,387; 5,028,435; 5,023,252; 5,000,956; 4,911,916; 4,898,734; 4,883,669; 4,882,377; 4,840,796; 4,818,540; 4,814,173; 4,806,341; 4,789,547; 4,786,277; 4,702,732; 4,690,683; 4,627,429; and 4,585,452, the disclosures of which are herein incorporated by reference.

Accordingly, pharmacological agent formulations suitable for oral administration in accordance with the subject invention may be present in discrete units, such as capsules, cachets, lozenges, tablets, and the like, each containing a predetermined amount of the active pharmacological agent; as a powder or granules; as a solution or a suspension in an aqueous or non-aqueous liquid; or as an oil-in-water or water-in-oil emulsion. As described above, such pharmacological agent formulations may be prepared by any suitable method of pharmacy which includes, but is not limited to, bringing into association the active pharmacological agent and a suitable carrier (which may contain one or more optional ingredients as noted above).

Pharmacological agents may be administered parenterally, such as intravenous (IV) administration, and may include a solution of the pharmacological agent dissolved in a pharmaceutically acceptable carrier. Among the acceptable vehicles and solvents that may be employed, include, but are not limited to, water and Ringer's solution, an isotonic sodium chloride, etc. In addition, sterile fixed oils may conventionally be employed as a solvent or suspending medium. For this purpose any bland fixed oil may be employed including synthetic mono- or diglycerides. In addition, fatty acids such as oleic acid can likewise be used in the preparation of injectables. Accordingly, a pharmacological agent may be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. These solutions are sterile and generally free of undesirable matter. These formulations may be sterilized by conventional, well known sterilization techniques.

For IV administration, the formulation may be a sterile injectable preparation, such as a sterile injectable aqueous or oleaginous suspension. This suspension may be formulated according to the known art using those suitable dispersing or wetting agents and suspending agents. The sterile injectable preparation may also be a sterile injectable solution or suspension in a nontoxic parenterally-acceptable diluent or solvent, such as a solution of 1,3-butanediol, and the like.

Accordingly, pharmacological agent formulations suitable for parenteral administration may include sterile aqueous and non-aqueous injection solutions of one or more active pharmacological agent agents, which preparations may be isotonic with the blood of the intended recipient. These preparations may contain buffers and solutes which render the formulation isotonic with the blood of the intended recipient. Aqueous and non-aqueous sterile suspensions may include suspending agents and thickening agents. The formulations may be presented in single- or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind described above.

Pharmacological agents may be delivered transdermally, by a topical route, formulated as applicator sticks, solutions, suspensions, emulsions, gels, creams, ointments, pastes, jellies, paints, powders, and aerosols. For example, embodiments may include a pharmacological agent formulation in the form of a discrete patch or film or plaster or the like adapted to remain in intimate contact with the epidermis of the recipient for a period of time. For example, such transdermal patches may include a base or matrix layer, e.g., polymeric layer, in which one or more pharmacological agent(s) are retained. The base or matrix layer may be operatively associated with a support or backing. As will be described in greater detail below, pharmacological agent formulations suitable for transdermal administration may also be delivered by electroporation or iontophoresis and may take the form of an optionally buffered aqueous solution of the pharmacological agent compound. Suitable formulations may include citrate or bis/tris buffer (pH 6) or ethanol/water and contain a suitable amount of active ingredient.

Pharmacological agents may also be administered by intranasal, intraocular, including insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995). For example, embodiments may also include at least one pharmacological agent in an aerosolized, atomized or nebulized vapor form, e.g., administrable via a metered dose device or nebulizer, and the like such that embodiments also include aerosolizing, vaporing or nebulizing one or more pharmacological agents for administration to a subject. Accordingly, the one or more pharmacological agent agents may be utilized in aerosol formulation or an analogous formulation to be administered via inhalation or analogous means. The one or more pharmacological agents employed in the practice of the present invention may be formulated into pressurized acceptable propellants such as dichlorodifluoromethane, propane, nitrogen and the like.

Pharmacological agents may also be administered in the form of suppositories for rectal or vaginal administration of the drug. These formulations may be prepared by mixing a pharmacological agent with a suitable non-irritating vehicle or excipient which is solid at ordinary temperatures but liquid at the rectal temperatures and will therefore melt in the rectum to release the drug. Such materials include, but are not limited to, cocoa butter, carbowaxes and polyethylene glycols. Embodiments include one or more pharmacological agent(s) made into suppositories by mixing with a variety of bases such as emulsifying bases or water-soluble bases.

Pharmacological agents may be delivered as microspheres for slow release in the body. For example, microspheres may be administered via intradermal injection of drug-containing microspheres, which slowly release subcutaneously (see Rao, *J. Biomater Sci. Polym. Ed.* 7:623-645, 1995); as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

Pharmacological agents may be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the pharmacological agent into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

Methods for preparing liposomal suspensions are known in the art and thus will not be described herein in great detail. Briefly, in those embodiments where the pharmacological agent is an aqueous-soluble pharmacological agent, the pharmacological agent may be incorporated into lipid vesicles using conventional liposome technology. In such instances, due to the water solubility of the pharmacological agent, the pharmacological agent may be substantially entrained within the hydrophilic center or core of the liposomes. The lipid layer employed may be of any conventional composition and may either contain cholesterol or may be cholesterol-free. When the pharmacological agent of interest is water-insoluble, the pharmacological agent may be substantially entrained within the hydrophobic lipid bilayer which forms the structure of the liposome employing conventional liposome formation technology. In either instance, the liposomes which may be produced may be reduced in size, as through the use of standard sonication and homogenization techniques. Embodiments of liposomal formulations containing the pharmacological agent of interest may be lyophilized to produce a lyophilizate which may be reconstituted with a pharmaceutically acceptable carrier, such as water, to regenerate a liposomal suspension.

Embodiments may also include administration of at least one pharmacological agent using a pharmacological delivery device such as, but not limited to, pumps (implantable or external devices), epidural injectors, syringes or other injection apparatus, catheter and/or reservoir operatively associated with a catheter, etc. For example, in certain embodiments a delivery device employed to deliver at least one pharmacological agent to a subject may be a pump, syringe, catheter or reservoir operably associated with a connecting device such as a catheter, tubing, or the like. Containers suitable for delivery of at least one pharmacological agent to a pharmacological agent administration device include instruments of containment that may be used to deliver, place, attach, and/or insert the at least one pharmacological agent into the delivery device for administration of the pharmacological agent to a subject and include, but are not limited to, vials, ampules, tubes, capsules, bottles, syringes and bags.

In representative embodiments, an agent delivery device specifically designed for delivery of agents to renal tissue is employed (i.e., a renal delivery device), where such renal delivery devices include, but are not limited to: those described in the following published PCT applications: WO 2004/032791; WO 2005/014100; WO 2005/002660; WO 2004/107965; WO 2005/091910; WO 2004/026370; WO 2004/030718; WO 2004/034767; WO 2004/026371

As noted above, in pharmaceutical dosage forms, a pharmacological agent of the subject invention may be administered alone or in appropriate association, as well as in combination, with other pharmaceutically active compounds. As used herein, "administered with" means that at least one pharmacological agent and at least one other adjuvant (including one or more other pharmacological agents) are administered at times sufficiently close that the results observed are indistinguishable from those achieved when one pharmacological agent and at least one other adjuvant (including one or more other pharmacological agents) are administered at the same point in time.

The pharmacological agent and at least one other adjuvant may be administered simultaneously (i.e., concurrently) or sequentially. Simultaneous administration may be carried out by mixing the at least one pharmacological agent and at least one other adjuvant prior to administration, or by administering the pharmacological agent and at least one other adjuvant at the same point in time. Such administration may be at different anatomic sites or using different routes of administration.

The phrases "concurrent administration," "administration in combination," "simultaneous administration" or "administered simultaneously" may also be used interchangeably and mean that the at least one pharmacological agent and at least one other adjuvant are administered at the same point in time or immediately following one another. In the latter case, the at least one pharmacological agent and at least one other adjuvant are administered at times sufficiently close that the results produced are synergistic and/or are indistinguishable from those achieved when the at least one pharmacological agent and at least one other adjuvant are administered at the same point in time. Alternatively, a pharmacological agent may be administered separately from the administration of an adjuvant, which may result in a synergistic effect or a separate effect. The methods and excipients described herein are merely exemplary and are in no way limiting.

Certain embodiments include administering an effective amount of a first agent and an effective amount of a second agent. For example, embodiments may include administering a first agent and a second agent to provide an enhanced therapeutic effect. By "enhanced therapeutic effect" is meant that at least the desired outcome occurs more quickly and/or is of greater magnitude with a combination of the pharmacological agents, as compared to the same doses of each component given alone; or that doses of one or all component(s) are below what would otherwise be a minimum effective dose (a "sub-MED").

Any two pharmacological agents may be given in close enough temporal proximity to allow their individual therapeutic effects to overlap. For example, embodiments of the subject invention include the co-timely administration of a first and second agent, where "co-timely" is meant administration of a second pharmacological agent while a first pharmacological agent is still present in a subject in a therapeutically effective amount. It is to be understood that in some instances this will require sequential administration. Alternatively, multiple routes of administration may be employed, e.g., intravenous or subcutaneous injection combined with oral administration, and the like.

Dosages

In determining the effective amount of a pharmacological agent to deliver for the treatment of a renal condition, the route of administration, the kinetics of the release system (e.g., pill, gel or other matrix), and the potency of the pharmacological agent are considered so as to achieve the desired therapeutic effect with minimal adverse side effects. The particular pharmacological agent employed may be administered to the subject being treated for a time period ranging from a day to a few weeks, consistent with the clinical condition of the treated subject however administration for periods of time longer than a few weeks, e.g., a few months, a year or more, even as long as the lifetime of a subject are also contemplated.

As noted above, the dose of pharmacological agent will be different for different subjects, condition(s) treated, etc. The following descriptions of exemplary embodiments describe average doses and may vary. Such descriptions are for exemplary purposes only and are in no way intended to limit the scope of the invention. For example, the number of capsules or tablets, teaspoonfuls of solution, and the like, administered depends at least in part on the strength of the particular pharmacological agent administered. Furthermore, the number of doses administered each day, the time allowed between doses, and the length of time a subject takes the medicine, etc., depend on the condition being treated, i.e., the condition for which a subject is taking the pharmacological agent.

Accordingly, in practicing embodiments of the subject methods, an effective amount of a pharmacological agent (or a plurality of pharmacological agents which may be the same or different type) may be administered to a subject to treat a condition affecting the subject such as renal failure. As noted above, the particular dosage, mode of administration, treatment times, etc., will vary according to a variety of factors, but may fall within the ranges conventionally administered for the particular pharmacological agent employed. As noted above, the dose of pharmacological agent will be different for different subject, condition(s) treated, etc. Exemplary treatment protocols are now provided.

Beta-Blocker

As noted above, embodiments may include administering an effective amount of a beta-blocker. Such embodiments may include administering adult oral dosage forms (capsules and tablets) of acebutolol ranging from about 200 milligrams (mgs.) to about 1200 mgs., e.g., from about 200 mgs. to about 800 mgs. Such oral dosages may be administered as a single dose one time a day, two times a day, or divided into two daily doses for an adult, etc.

Embodiments may include administering atenolol. Such embodiments may include administering adult oral dosage forms (e.g., tablets) of atenolol (e.g., available under the brand name TENORMIN) that range from about 25 mgs. to about 100 mgs. once a day. For example, administration may include about 50 mgs. once a day, or about 100 mgs. of atenolol once a day, or about 50 mgs. atenolol two times a day, e.g., for about six to about nine days. Embodiments that include administering atenolol in adult injection dosage forms may include about 5 mgs. given over 5 minutes, repeated ten minutes later. Atenolol may also be administered intravenously in certain embodiments.

Embodiments may include administering adult oral dosage forms (e.g., tablets) of betaxolol to treat a condition. Such embodiments may include administering about 10 mgs. of betaxolol as an adult dosage form once a day.

Embodiments may include administering adult oral dosage forms (e.g., tablets) of bisoprolol (e.g., available under the brand name ZEBETA). Such embodiments may include administering about 5 mgs. to about 10 mgs. of bisoprolol as an adult oral dosage forms (e.g., tablets) once a day.

Embodiments may include administering adult oral dosage forms (e.g., tablets) of carteolol. Adult oral dosage forms (e.g., tablets) of carteolol may include about 0.5 mgs. to about 10 mgs. administered once a day.

Embodiments may include administering esmolol. Esmolol may be administered via iv as follows: loading dose of about 20-30 mg ivp over 1 minute using a 10 mg/ml 10 ml vial and maintenance dose of about 2 To 12 mg/min as titrated to patient response and maintenance infusions may be increased by about 2 to 3 mg/min at 10 minute intervals until the desired response is achieved.

Embodiments may include administering adult oral dosage forms (e.g., tablets) of labetalol. Adult oral dosage forms (e.g., tablets) of labetalol may include about 100 mgs. to about 400 mgs. two times a day. Adult injection dosage forms may include about 20 mgs., e.g., injected slowly over about two minutes with additional injections of about 40 mgs. and about 80 mgs. given about every ten minutes if needed, up to a total of about 300 mgs., instead as an infusion at a rate of about 2 mgs. per minute to a total dose of about 50 mgs. to about 300 mgs.

Embodiments may include administering adult oral dosage forms (e.g., tablets) of metoprolol. Adult oral dosage forms (e.g., tablets) of metoprolol may include about 100 mgs. to 450 mgs. a day, taken as a single-dose or in divided doses. For example, embodiments may include administering about 50 mgs. about every six hours for about 24 hours or more and then about 100 mgs. two times a day for about 1 to about 3 months or more, e.g., from about 1 to about 3 years or more. Embodiments may include administering long-acting adult oral dosage forms (extended-release tablets) that may include up to about 400 mgs. once a day. Adult injection dosage forms may include about 5 mgs. every two minutes for about three doses.

Embodiments may include administering adult oral dosage forms (e.g., tablets) of nadolol. Embodiments may include administering adult oral dosage forms (e.g., tablets) of nadolol that may include about 40 mgs. to about 320 mgs. once a day.

Embodiments may include administering adult oral dosage forms (e.g., tablets) of oxprenolol. Embodiments may include administering adult oral dosage forms (e.g., tablets) of oxprenolol (short-acting) that may include about 20 mgs. three times a day. Embodiments may include administering adult long-acting oral dosage forms (extended-release tablets) that may include about 120 mgs. to about 320 mgs. once a day.

Embodiments may include administering adult oral dosage forms (e.g., tablets) of pentbutolol. Embodiments may include administering adult oral dosage forms (e.g., tablets) of penbutolol that may include about 20 mgs. once a day.

Embodiments may include administering adult oral dosage forms (e.g., tablets) of pindolol. Embodiments may include administering adult oral dosage forms (e.g., tablets) of pindolol that may include about 5 mgs. two times a day—up to about 60 mgs. a day.

Embodiments may include administering adult oral dosage forms (e.g., tablets) of propranolol. Embodiments may include administering adult oral dosage forms (e.g., tablets) of propranolol that may include, for regular (short-acting) oral dosage forms (tablets and oral solution), about 80 mgs. to about 320 mgs. a day taken in two, three, or four divided doses up to about 640 mgs./day in certain embodiments. Embodiments may also include about 10 mgs. to about 40 mgs. three or four times a day for an adult and about 500 micrograms (0.5 mgs.) to about 4 mgs. per kilogram of body weight a day taken in divided doses for children. Embodiments may include administering long-acting adult oral dosage forms (extended-release capsules) that may include about 80 mgs. to about 320 mgs. once a day up to about 640 mgs. once a day. Embodiments may include administering adult injection dosage forms that range from about 1 mg. to about 3 mgs. given at a rate not greater than about 1 mg per minute. The dose may be repeated after about two minutes and again after about four hours if needed. Children may be administered about 10 mgs. to about 100 micrograms (0.01 to 0.1 mg) per kilogram of body weight given intravenously about every six to eight hours.

Embodiments may include administering adult oral dosage forms (e.g., tablets) of sotalol. Embodiments may include administering adult oral dosage forms (e.g., tablets) of sotalol that may include about 80 mgs. two times a day up to about 320 mgs. per day taken in two or three divided doses.

Embodiments may include administering adult oral dosage forms (e.g., tablets) of timolol. Embodiments may include administering adult oral dosage forms (e.g., tablets) of timolol that may include about 10 mgs. two times a day up to about 60 mgs. per day taken as a single dose or in divided doses. For example, up to 30 mgs. once a day or in divided doses.

Aldosterone Antagonists

Embodiments may include administering an aldosterone antagonist. For example, embodiments may include administering adult oral dosage forms (e.g., tablets) of spironolactone that may range from about 50 mgs. to about 400 mgs. daily. Embodiments may include administering adult oral dosage forms (e.g., tablets) of eplerenone that may range from about 50 mgs. to about 100 mgs. daily.

Angiotensin II Receptor Blockades

Embodiments may include administering an angiotensin II receptor blockade. Such embodiments may include administering an adult oral dosage form of candesartan (e.g., ATACAND) to a subject to treat a condition. Exemplary treatment protocols may include administering about 2 mgs. to about 32 mgs. of candesarten daily (i.e., for a 24 hour interval), e.g., about 16 mgs. daily. Embodiments may include administering adult oral dosage forms of irbersarten (e.g., AVAPRO) to a subject to treat a condition. Exemplary treatment protocols may include administering about 75 mgs. to about 100 mgs. or more, e.g., up to about 300 mgs., of irbersarten daily. Embodiments may include administering adult oral dosage forms of losartan (e.g., COZAAR) to a subject to treat a condition. Exemplary treatment protocols may include administering about 25 mgs. to about 50 mgs. or more, e.g., 100 milligrams, of losartan orally once daily or twice daily. Embodiments may include administering adult oral dosage forms of telmisartan (e.g., MICARDIS) to a subject to treat a condition. Exemplary treatment protocols may include administering about 20 mgs. to about 80 mgs. of telmisartin daily. Embodiments may include administering adult oral dosage forms of valsartan (e.g., DIOVAN) to a subject to treat a condition. Exemplary treatment protocols may include administering about 20 mgs. to about 80 mgs. of valsarten once daily. Embodiments may include administering adult oral dosage forms of eprosarten (e.g., TEVETAN) to a subject to treat a condition. Exemplary treatment protocols may include administering about 400 mgs. to about 800 mgs. of eprosarten once daily or twice daily.

Angiotensin Converting Enzyme Inhibitors (ACE Inhibitors)

Embodiments may include administering an ACE inhibitor. Such may include administering adult oral dosage forms of captopril (e.g., CAPOTEN) to a subject to treat a condition. Exemplary treatment protocols may include administering about 12.5 mgs. to about 50 mgs. of captopril over about 8 to about 12 hours. Embodiments may include administering adult oral dosage forms of enalapril (e.g., VASOTEC) to a subject to treat a condition. Exemplary treatment protocols may include administering about 5 mgs. to about 20 mgs. of enalapril once daily. Embodiments may include administering adult-oral dosage forms of fosinopril (e.g., MONOPRIL) to a subject to treat a condition. Exemplary treatment protocols may include administering about 10 mgs. to about 80 mgs., e.g., about 20 mgs. to about 40 mgs., of fosinopril daily. Embodiments may include administering adult oral dosage forms of lisinopril (e.g., PRINIVIL) to a subject to treat a condition. Exemplary treatment protocols may include administering about 10 mgs. to about 80 mgs., e.g., about 20 mgs. to about 40 mgs., of lisinopril daily. Embodiments may include administering adult oral dosage forms of moexipril (e.g., UNIVASC) to a subject to treat a condition. Exemplary treatment protocols may include administering about 3.75 mgs. to about 15 mgs., e.g., 7.5 mgs. of moexipril daily. Embodiments may include administering adult oral dosage forms of quinaapril (e.g., ACCUPRIL) to a subject to treat a condition. Exemplary treatment protocols may include administering about 10 mgs. to about 80 mgs, e.g., about 20 mgs., of quinapril once daily. Embodiments may include administering adult oral dosage forms of ramipril (e.g., ALTACE) to a subject to treat a condition. Exemplary treatment protocols may include administering about 2.5 mgs. to about 20 mgs. of ramipril daily. Embodiments may include administering adult oral dosage forms of trandolapril (e.g., MAVIK) to a subject to treat a condition. Exemplary treatment protocols may include administering about 1 mg. to about 4 mgs., e.g., about 2 mgs., of trandolapril daily.

Sympathomimetics

Embodiments may include administering a sympathomimetic. For example, embodiments may include administering trimethaphan via an I.V., e.g., about 0.1 mgs. to about 1.0 mgs./minute, up to about 15 mgs. per minute. Embodiments may include administering by mouth clonidine at about 0.1 mgs. to about 2.4 mgs. daily. Embodiments may include administering by mouth reserpine at about 10 mgs. to about 20 mgs. daily. Embodiments may include administering by mouth guanethidine at about 10 mgs. to about 50 mgs. daily.

Calcium Channel Blockers:

Embodiments may include administering a calcium channel blocker. Embodiments may include orally administering amlodipine besylate (e.g., available under the brand name NORVASC), e.g., about 5 mgs. to about 20 mgs. daily; diltiazem hydrochloride (e.g., available under the brand names CARDIZEM CD, CARDIZEM SR, DILACOR XR, TIAZAC) at about 30 mgs. to about 360 mgs. four times per day (for example 180 mgs. to about 360 mgs. divided into four times per day); felodipine at about 2.5 mgs. to about 10 mgs. daily; isradipine (e.g., available under the brand names DYNACIRC, DYNACIRC CR) at about 2.5 mgs. daily; nicardipine (e.g., available under the brand name CARDENE SR) at about 20 mgs. to about 40 mgs. three times per day; nifedipine (e.g., available under the brand names ADALAT CC, PROCARDIA XL) at about 10 mgs. three times per day; nisoldipine (e.g., available under the brand name SULAR) at about 10 mgs. to about 20 mgs. daily; and verapamil hydrochloride (e.g., available under the brand names CALAN SR, COVERA HS, ISOPTIN SR, VERELAN) at about 40 mgs. three times per day.

Sodium Channel Blockers

Embodiments may include administering a sodium channel blocker. For example, embodiments may include administering about 150 mgs. of propafenone by mouth every 8 hours (450 mgs./day) up to about 300 mgs. every 8 hours (90 mgs./day). Embodiments may also include administering about 50 mgs. to about 100 mgs. of flecainide by mouth about every 12 hours up to about 400 mgs./day. Embodiments may also include administering about 400 mgs. to about 2400 mgs. of tocainide by mouth about every 8 hours. Embodiments may also include administering about 100 mgs. to about 200 mgs. of phenyloin by mouth three times per day. Embodiments may also include administering about 10-30 mgs of about 1% to about 2% lidocaine IM (the maximum individual dosage typically should not exceed about 4.5 mg/kg of body weight and generally the maximum total dose should not exceed about 300 mgs.). Embodiments may also include administering about 150 mgs. to about 300 mgs. of disopyramide by mouth about every 6 hours to about every 12 hours, up to about 1600 mgs. per day. Embodiments may also include administering quinidine (e.g., available under the brand name QUINAGLUTE) at about two tablets (648 mgs.; 403 mgs. of quinidine base) of QUINAGLUTE by mouth about every 8 hours.

Glucocorticoid Receptor Blockers

Embodiments may include administering a glucocorticoid receptor blocker. For example, embodiments may include administering mifepristone by mouth at about 400 micrograms to about 600 mgs.

Peripheral Andrenergic Inhibitors

Embodiments may include administering a peripheral andrenergic inhibitor. For example, embodiments may include administering about 5 mgs. to about 75 mgs. of guanadrel (e.g., available under the brand name HYLOREL) by mouth e.g., about 5 mgs. two times per day, about 20 to about 75 mgs. per day in divided doses. Embodiments may also include administering about 10 mgs. to about 50 mgs. or more per day of guanethidine monosulfate (e.g., available under the brand name ISMELIN) by mouth. Embodiments may also include administering about 0.05 to about 1.5 mgs. once per day by mouth of reserpine (e.g., available under the brand names SERPASIL, MECAMYLAMINE, HEXEMETHONIUM). Embodiments may also include administering about 2.5 mgs. of mecamylamine two times per day by mouth.

Blood Vessel Dilators

Embodiments may include administering a blood vessel dilator. For example, embodiments may include administering about 10 mgs. to about 50 mgs. of hydralazine hydrocholoride (e.g., available under the brand name APRESOLINE) by mouth four times a day. Embodiments may also include administering about 5 mgs. to about 40 mgs. of minoxidil (e.g., e.g., available under the brand name LONITEN) by mouth once per day.

Central Agonists

Embodiments may include administering a central agonist. For example, embodiments may include administering about 250 mgs. of alpha methyldopa (e.g., available under the brand name ALDOMET) by mouth three times per day or about 500 mgs. to about 2 grams per day divided into 2 to 4 doses. Embodiments may also include administering about 0.1 mgs. to about 0.6 mgs. of clonidine hydrochloride (e.g., available under the brand name CATAPRES) by mouth once per day. Embodiments may also include administering about 4 mgs. of guanabenz acetate (e.g., available under the brand name WYTENSIN) by mouth two times per day (up to about 32 mgs. per day). Embodiments may also include administering about 1 mg. to about 3 mgs. of guanfacine hydrochloride (e.g., available under the brand name TENEX) by mouth once per day.

Combined Alpha and Beta-Blockers

Embodiments may include administering a combined alpha and beta-blocker. For example, embodiments may include administering about 100 mgs. two times per day of labetolol hydrochloride (e.g., available under the brand names NORMODYNE, TRANDATE) by mouth up to about 400 mgs. per day. Embodiments may also include administering about 3.125 mgs. two times per day of carvedilol (e.g., available under the brand name COREG) by mouth up to about 50 mgs. per day.

Alpha Blockers

Embodiments may include administering an alpha and beta-blocker. For example, embodiments may include administering about 1 mg once per day by mouth of doxazosin mesylate (e.g., available under the brand name CARDURA) up to about 16 mgs. per day. Embodiments may also include administering about 0.5 mgs. by mouth of prazosin hydrochloride (e.g., available under the brand name MINIPRESS) two or three times per day (and may include about 6 to about 15 mgs. per day divided into 2 or 3 doses. Embodiments may also include administering about 1 mg. of terazosin hydrochloride (e.g., available under the brand name HYTRIN) by mouth once per day, up to about 5 mgs. per day.

Combination Diuretics

Embodiments may include administering a combined diurentic. For example, embodiments may include administering about 1-2 tablets of amiloride hydrochloride+hydrochlorothiazide (e.g., available under the brand name MODURETIC) once per day for tablets containing 5 mgs. of anhydrous amiloride HCl and 50 mgs. of hydrochlorothiazide). Embodiments may also include administering about 25 mgs. to about 50 mgs. once per day by mouth of spironolactone+hydrochlorothiazide (e.g., available under the brand name ALDACTAZIDE). Embodiments may also include administering about 1 to 2 tablets one per day of triamterene+hydrochlorothiazide (e.g., available under the brand names DYAZIDE, MAXZIDE) for tablets containing 25 mgs. hydrochlorothiazide and 37.5 mgs. triaterene.

Potassium Sparing Diuretics

Embodiments may include administering a potassium sparing diuretic. For example, embodiments may include administering about 5 mgs. to about 20 mgs. by mouth once per day of amiloride hydrochloride (e.g., available under the brand name MIDAMAR). Embodiments may also include administering about 25 mgs. to about 200 mgs. once per day by mouth of spironolactone (e.g., available under the brand name ALDACTONE). Embodiments may also include administering about 1 to 2 tablets once per day of triamterene (e.g., available under the brand name DYRENIUM)) for tablets containing 25 mgs. hydrochlorothiazide and 37.5 mgs. triamterene.

Nitrate Compounds

Embodiments may include administering a nitrate or nitrate compound. For example, embodiments may include administering isosorbide dinitrate (e.g., available under the brand name ISODIL) at about 50 to about 40 mgs. orally four times per day or 40 mgs. sustained release orally every 8 to 12 hours. Embodiments may also include administering isosorbide mononitrate (e.g., available under the brand names ISMO, MONOKET) at about 20 mgs. orally two times per day and/or may include administering extended release initially about 30 mgs. to about 60 mgs. orally once per day. Maximum of about 240 mgs./day. Embodiments may also include administering nitroglycerine ointment, e.g., about 0.5 inches q8 h and/or about 0.5 to about 2 inches every 4 to 6 hours, maximum 4 inches every 4 to 6 hours (0.5 inches is about 7.5 mgs.). Embodiments may also include administering nitrobid, e.g., orally about 2.5 mgs. to about 9 mgs. 2 to 4 times per day. Embodiments may also include administering a nitroglycerin patch, e.g., one patch each day applied and removed at bedtime.

Vasopressin Inhibitors

Embodiments may include administering a vasopressin. For example, embodiments may include administering about up to about 6.75 mg administered via IV of atosiban, e.g., 300 micrograms/min to about 100 micrograms/min IV.

Oxytocin Inhibitors

Embodiments may include administering an oxytoxin inhibitor. For example, embodiments may include administering about 0.25 to about IM of terbutaline, typically not more than about 0.5 mgs. within a four hour period. Embodiments may also include administering about 50 micrograms per minute IV of ritodrine, maximum dosage of about 300 micrograms per minute.

Renin Inhibitors

Embodiments may include administering a rennin inhibitor. For example, embodiments may include administering Aliskiren by mouth at about 2 mgs to about 10 mgs./day.

Vesicular Monoamine Transport (VMAT) Inhibitors

Embodiments may include administering a VMAT inhibitor. For example, embodiments may include administering tetrabenazine by mouth at about 150 mgs. to about 200 mgs. once per day. Embodiments may also include administering reserpine at about 50 micrograms to about 500 micrograms one time per day.

Applying Electrical Energy

As noted above, certain embodiments include employing electrical modulation, in a manner effective to cause the desired treatment of a renal condition according to the subject methods. By "electrically modulating at least a portion of a subject's autonomic nervous system" is meant altering or changing at least a portion of an autonomic nervous system by electrical means to provide a change, alteration or shift in at least one component or aspect of the autonomic nervous system. Certain embodiments include electrically stimulating, e.g., with long-term low frequency stimulation, to inhibit or depress activity in the sympathetic nervous system.

Any suitable area may be targeted for electrical modulation. Areas that may be targeted include, but are not limited to, pre- and post ganglionic nerve fibers, as well as ganglionic structures, efferent and afferent nerve fibers, synapses, etc., and combinations thereof in certain embodiments. In certain embodiments, activity in a given nerve fiber may be electrically modulated in more than one area of the nerve fiber. In certain embodiments, electrical energy is applied to modulate synaptic efficiency, e.g., to increase or decrease the sensitivity of a synapse and include modulating presynaptic neurons.

As such, areas which may be targeted with electrical energy include, but are not limited to, pre- and post ganglionic nerve fibers, ganglionic structures, efferent and afferent nerve fibers, the hypothalamus, receptors any receptor described herein, afferent autonomic nerves (sympathetic and parasympathetic). Embodiments include receptors of the hypothalamus, including hormonal receptors on the hypothalamus. In certain embodiments, a given nerve fiber or the like may be targeted for electrical modulation in more than one area of the nerve fiber. Targeted areas of the nervous system which may be targeted in accordance with the subject invention include, but are not limited to, vagus nerve, otic ganglion, and sphenopalatine ganglion, internal carotid nerve and plexus, middle and superior cervical sympathetic ganglion; vertebral ganglion; cervicothoracic ganglion; sympathetic trunk; cervical cardiac nerves; cardiac plexus; thoracic aortic plexus; celiac ganglion; celiac trunk and plexus; superior mesenteric ganglion; superior mesenteric artery and plexus; intermesenteric plexus; inferior mesenteric ganglion; inferior mesenteric artery and plexus; superior hypogastric plexus; hypogastric nerves; vesical plexus; thoracic cardiac nerves; sympathetic trunk; 6th thoracic sympathetic ganglion; gray and white rami communicantes; greater, lesser and least splanchnic nerves; aorticorenal ganglion; lumbar splanchnic nerves; gray rami communicantes and sacral splanchnic nerves; and the like, or a combination of two or more of the above.

A number of different devices may be employed in accordance with the subject invention. For example, device and systems for applying electrical energy to a subject and which may be adapted for use in the subject invention are described, e.g., in copending U.S. Patent application Ser. Nos. 10/661,368, 10/871,366 and elsewhere, the disclosures of the US patent applications are herein incorporated by reference. Such devices may be positioned directly on a targeted area, e.g., positioned below the skin of a subject directly on or adjacent a portion of the nervous system (e.g., one or more nerve fibers) such as an implantable device, or may be an external device (i.e., some or all of the device may be external to the subject). In accordance with the subject invention, one or more electrodes or electrical contacts may be positioned directly on or adjacent a targeted area, where the one or more electrodes may be surgically implanted, e.g., directly on or adjacent a targeted nerve fiber of a subject. In certain embodiments, an immunomodulator such as a steroid or the like, may be incorporated into a surface contacting area of a device, e.g., to minimize inflammation of the targeted site.

An electric energy applying device typically includes a stimulator such as an electrode, a controller or programmer and one or more connectors for connecting the stimulating device to the controller. In certain embodiments more than one electrode may be employed. In further describing representative electrodes, such are described in the singular, but it will be apparent that more than one electrode may be used, where such may be the same or may be different in one or more aspects. Accordingly, the description of an exemplary electrode suitable for use in the subject methods is applicable to other electrodes that may be employed.

The electrode employed in the subject invention is controllable to provide output signals that may be varied in voltage, frequency, pulse width, current and intensity. The electrode may be one that provides both positive and negative current flow from the electrode and/or may be capable of stopping current flow from the electrode and/or changing the direction of current flow from the electrode. For example, embodiments include an electrode that is controllable in these respects, i.e., controllable in regards to producing positive and negative current flow from the electrode, stop current flow from the electrode, change direction of current flow from the electrode, and the like. In certain embodiments, the electrode has the capacity for variable output, linear output and short pulse width.

The energy source for the electrical output may be provided by a battery or generator such as a pulse generator that is operatively connected to the electrode. The energy source may be positioned in any suitable location such as adjacent to the electrode (e.g., implanted adjacent the electrode), or a remote site in or on the subject's body or away from the subject's body in a remote location and the electrode may then be connected to the remotely positioned energy source using wires, e.g., may be implanted at a site remote from the electrode or positioned outside the subject's body in certain instances. Of interest are implantable generators analogous to a cardiac pacemaker.

The electrode may be mono-polar, bipolar or multi-polar. In order to minimize the risk of an immune response triggered by the subject against the device and minimize damage such as corrosion and the like to the device from other biological fluids, etc., the electrode and any wires and optional housing materials are made of inert materials such as for example silicon, metal, plastic and the like. For example, a multi-polar electrode having about four exposed contacts (e.g., cylindrical contacts may be employed).

A controller or programmer may also be coupled with an electric energy applying device. The programmer is typically one or more microprocessors under the control of a suitable software program. Other components of the programmer will be apparent to those of skill in the art, e.g., analog to digital converter, etc.

The electric energy applying device may be pre-programmed for desired parameters. In certain embodiments the parameters are controllable such that the electrode signal may be remotely modulated to desired settings without removal of the electrode from its targeted position. Remote control may be performed, e.g., using conventional telemetry with an implanted electric signal generator and battery, an implanted radiofrequency receiver coupled to an external transmitter, and the like. In certain embodiments, some or all parameters of the electrode may be controllable by the subject, e.g., without supervision by a physician. For example, a magnetic signal may be employed. In such embodiments, one or more magnets may be employed such that upon bringing a magnet in proximity to or away from the power source such as a pulse generator, the magnet may be employed to interfere with the electronic circuitry thus modulating the power—either increasing or decreasing the power supplied depending on whether the magnet is brought in proximity or moved away from the power source.

FIG. 1 shows an exemplary embodiment of an electric energy applying device 100. Device 100 may be implanted in a suitable position of a subject's body 10. One or more leads 23 are shown positioned to stimulatory or inhibitory electrical energy. Device 100 include energy source 14 which may take the form of a modified signal generator Model 7424 manufactured by Medtronic, Inc. under the trademark Intrel II. Lead 23 may take the form of any suitable lead, such as any of the leads that are sold with the Model 7427 and is coupled to energy source 14 by one or more conventional conductors 16 and 18. Lead 23 may include a paddle lead, a lead having one or more electrodes and/or catheters, or a combination catheter/lead capable of providing electrical impulses and pharmacological delivery. In certain embodiments, a lead may be composed of concentric tubes such as made of platinum or other like material. The tubes may be coated with a polymer except for the distal portions that may serve as the electrodes. Conductive wires carrying energy to the electrodes may be in the interior of the concentric tubes. Optionally, a distal electrode end may include a small recording microelectrode to help assist in the actual placement of the lead.

The present invention may be operated as an open-loop controlled system. In an open-loop system, the physician or patient may at any time manually or by the use of pumps or motorized elements adjust treatment parameters such as pulse amplitude, pulse width, pulse frequency, or duty cycle. Optionally, the present invention may incorporate a closed-loop control system which may automatically adjust the electrical parameters in response to a sensed parameter or condition of a subject. Under a closed-loop feedback system to provide automatic adjustment of parameters of the electrodes, a sensor that senses a condition of the body is utilized. More detailed descriptions of sensors that may be employed in the practice of the subject invention, and other examples of sensors and feedback control techniques that may be employed are disclosed in U.S. Pat. No. 5,716,377, which is incorporated herein by reference.

As shown in FIG. 1, the distal end of lead 23 terminates in one or more delivery elements such as stimulation electrodes which may be implanted using conventional surgical techniques. The type of treatment that is desired determines the location of the electrodes. Any number of electrodes may be used for various applications. Each of the electrodes may be individually connected to energy source 14 through lead 23 and conductors 16 and 18. Lead 23 may be surgically implanted either by a laminotomy or by a needle.

Energy source or signal generator 14 may be programmed to provide a predetermined stimulation (or inhibition) dosage in terms of pulse amplitude, pulse width, pulse frequency, or duty cycle. As shown, a programmer 20 may be utilized to provide stimulation (or inhibition) parameters to the delivery device via any suitable technology, e.g., using telemetry and the like. For example, in using telemetry, programmer 20 may be coupled to an antenna 24 via conductor 22. In certain embodiments, the programmer may be positioned, e.g., implanted, inside body 10. For example, in certain embodiments the programmer may be integrated with the energy source, electrode, etc., for example as a single unit.

Device 100 may optionally include one or more sensors to provide closed-loop feedback control of the treatment and/or electrode positioning. One or more sensors (not shown) may be attached to or implanted into a portion of a subject's body suitable for detecting a physical and/or chemical indicator of the subject. For example, sensing feedback may be accomplished, e.g., by a mechanical measure within a lead or an ultrasound or other sensor to provide information about the treatment parameters, lead positioning, LTP, etc.

Operative placement of a suitable electric energy applying device may be accomplished using any suitable technique. An electrode introducer needle may be employed to implant the electrode on or proximate to the area of interest. The size of the introducer needle may vary depending on the diameter of the electrode, etc., where in certain embodiments the electrode introducer needle may be a 12-gauge, 14-gauge, 16-gauge, 18-gauge, 20-gauge needle or 22-gauge needle, e.g., an electrode introducer needle available from Radionics in the Sluyter-Mehta kit as SMK 100 mm 2 mm active tip cannula. However, it should be understood that other electrode introducer needles may be used as appropriate to the needs and skill level of the practitioner performing the surgical procedure.

At least one imaging apparatus such as a CT scan, MRI apparatus, ultrasound apparatus, fluoroscope, or the like, may be employed to monitor the surgical. For exemplary purposes only, the subject method will be described using a fluoroscope, where such is in no way intended to limit the scope of the invention. The subject is placed in a suitable position for access e.g., supine, on a fluoroscopy table, with the patient's nose pointing vertically. The fluoroscope is then adjusted to a straight lateral position. And the entry point for the insertion of the electrode is determined.

Once the entry point is determined, the skin overlying the entry point is shaved and prepared with antiseptic solution. A 25-gauge needle may be used to inject a subcutaneous local anesthetic (such as, for example, 2 cc of 2% lidocaine) into the skin and subcutaneous tissues overlying the entry point. In addition to the local anesthetic, the patient may be given intravenous sedation and prophylactic antibiotics prior to commencement of the implantation procedure if desired.

The electrode introducer needle is inserted at the entry point and advanced. The fluoroscope may be adjusted as the needle is advanced. Once the needle is positioned the stylet is withdrawn from the electrode introducer needle. Once the implanted electrode is in place, the end of the electrode that is outside the skin is carefully held in place against the skin. The electrode introducer needle may then be slowly removed, leaving the implanted electrode in place. At this point, if desired, a few small subcutaneous sutures may be placed around the electrode to hold it in the desired position.

Once the needle has been completely removed and the implanted electrode is in the final position, then the proximal part of the electrode that is coming out of the skin may be secured to the skin of the subject, e.g., by adhesive tape. Additionally, a small incision may be made on the skin at the area the electrode exits the face. Then several subcutaneous sutures may be placed around the electrode to hold it in place. The distal end of the electrode may then be connected to an extension wire or catheter, which is tunneled to the subclavicular area, or another region which will house the device used as an energy source for the implanted electrode. The device or devices used to control the electrode may be surgically implanted in the desired region by procedures known in the art, such as have been applied in surgical neuromodulation therapies used to treat Parkinson's disease.

In certain embodiments of the subject invention, an electrode may be utilized which, instead of or in addition to delivering electric impulses to at least a portion of the autonomic nervous system, delivers a pharmacological agent to at least a portion of the autonomic nervous system. For example, an electrode may be used that has a small port at its tip which is connected to a reservoir or pump containing a pharmacological agent. The pharmacological agent delivery electrode may be implanted using an analogous procedure as that described above for the autonomic system modulating-electrode. In certain embodiments the reservoir or pump may also be implanted in the subject's body, analogous to that described above for the electrical impulse generator. The pharmacological agent delivery electrode may be controllable such that the amount of pharmacological agent delivered, the rate at which the pharmacological agent may be delivered, and the time period over which the pharmacological agent is delivered may be adjusted.

In embodiments in which electrical energy is used, any suitable protocol may be used, where certain protocols include using an electric energy applying device to deliver a suitable amount of electrical energy to a subject. Once an electric energy applying device is positioned in a suitable position on or about one or more targeted areas electrical energy is applied thereto for a period of time sufficient to provide the desired effect. This period of time will vary depending on the area (e.g., the nerve fiber) being treated, the condition being treated, etc. Certain embodiments include simultaneously monitoring (i.e., in "real time") the as aspect of the nervous system such that a given nerve fiber may be electrically stimulated (or electrically inhibited) until the desired result is observed. Still further, in many embodiments once the desired result is achieved, a targeted area may be repeatedly electrically stimulated (or inhibited) one or more times to maintain the desired state such that the subject methods may be repeated one or more times, i.e., the subject methods include chronically applying electrical energy to a subject, such as chronically applying electrical energy to one or more nerve fibers. For example, in certain embodiments electrical stimulation (e.g., intermittent mild electrical pulses) may be delivered to a given area of the nervous system, twenty-four hours a day for a period of days, weeks, months, or even years in certain embodiments.

During the period of time that electrical energy is applied to a given area, the electrical energy may be substantially continuous, including continuous or intermittent (i.e., pulsed or periodic), where in many embodiments the electrical energy is in the form of electrical pulses. In other words, in certain embodiments electrical energy may be given continuously during the above-described period of time and in certain embodiments electrical energy may be given to an area in a pulsed or intermittent manner during the period of time described above.

In accordance with the subject methods to apply electrical energy to a subject, once operatively positioned the electric energy applying device is activated to provide an electrical signal to the targeted area in a manner effective to practice the subject methods.

In practicing the subject methods, activation of the electric energy applying device directly applies the electrical output of the device, i.e., electrical impulses, to the targeted area. The exact parameters of the applied electrical energy may vary depending on the particular subject, condition being treated, etc. For example, an electronic current wave may be provided when the electrical energy is applied. In certain embodiments, the current wave includes current waves of high frequency, e.g., high frequency pulses, where the current wave may also include low frequency amplitude modulation. In certain embodiments, a plurality of high frequency bursts of current pulses may be applied in addition to the application of underlying low frequency continuous stimulus. Stimulation may be monopolar or multipolar.

For example, to stimulate a targeted area, voltage or intensity may range from about 1 millivolt to about 1 volt or more, e.g., 0.1 volt to about 50 volts, e.g., from about 0.2 volt to about 20 volts and the frequency may range from about 1 Hz to about 2500 Hz, e.g., about 1 Hz to about 1000 Hz, e.g., from about 2 Hz to about 100 Hz in certain embodiments. In certain embodiments a pure d-c voltages may be employed. The pulse width may range from about 1 microsecond to about 2000 microseconds or more, e.g., from about 10 microseconds to about 2000 microseconds, e.g., from about 15 microseconds to about 1000 microseconds, e.g., from about 25 microseconds to about 1000 microseconds. The electrical output may be applied for at least about 1 millisecond or more, e.g., about 1 second, e.g., about several seconds, where in certain embodiments the stimulation may be applied for as long as about 1 minute or more, e.g., about several minutes or more, e.g., about 30 minutes or more may be used in certain embodiments.

In certain embodiments, a control feedback loop is provided. For example, during or following a particular electric energy applying protocol, a biological aspect of a subject may be monitored, e.g., by sensing conduction in a neuronal system, e.g., in a particular electrically stimulated nerve fiber, or by any suitable method. For example, a sensor suitable for detecting nerve cell or axon activity may be implanted in a portion of a subject's body. A sensor may take the form of an electrode or the like. Signals received by such a sensor may be amplified before further processing. A sensor may also take the form of a device capable of detecting nerve compound action potentials or may take the form of a transducer that includes an electrode with an ion selective coating applied which is capable of directly transducing the amount of a particular transmitter substance or its breakdown by-products. In utilizing a feedback system, if a predetermined detection criteria is not detected the same or a different stimulus protocol may be performed and may be automatically initiated under the control of a controller. For example, in those instances where a different protocol is performed, one or more of the electrical energy applying parameters may be modified, e.g., the pulse width may be increased, or the like, in the second protocol.

Utility

The subject methods find use in a variety of applications in which it is desired to treat a subject for a renal associated condition, e.g., a renal condition that may be influenced by an abnormality in the subject's autonomic nervous system (e.g., a sympathetic bias). In such methods, at least a portion of a subject's autonomic nervous system is modulated in a manner suitable to treat the subject for the condition, e.g., in a manner to increase the parasympathetic activity/sympathetic activity ratio or decrease the parasympathetic activity/sympathetic activity ratio in certain embodiments, e.g., as applied to a kidney.

The subject methods find use in the treatment of a variety of different renal associated conditions in which an abnormality in a subject's autonomic nervous system exists. By treatment is meant both a prevention and/or at least an amelioration of the symptoms associated with the condition afflicting the subject is achieved, where amelioration is used in a broad sense to refer to at least a reduction in the magnitude of a parameter, e.g., symptom, associated with the renal condition being treated. As such, treatment also includes situations where the condition, or at least symptoms associated therewith, are completely inhibited, e.g. prevented from happening, or stopped, e.g. terminated, such that the subject no longer suffers from the renal associated condition, or at least the symptoms that characterize the condition. In certain embodiments, the condition being treated is a renal disease.

As noted above, abnormalities in a subject's autonomic nervous system include those characterized by an abnormally high parasympathetic activity or abnormally low parasympathetic activity and/or an abnormally high sympathetic activity or abnormally low sympathetic activity. Certain abnormalities may be characterized by having normal activity in one of the systems of the autonomic nervous system (the parasympathetic system or sympathetic system), but which may have abnormal activity in the other system (the parasympathetic system or sympathetic system).

The subject methods find use in the treatment of a variety of different renal associated conditions, including, but not limited to: acute and chronic renal failure, contrast nephropathy (e.g., iodine-based contrast nephropathy), cardiorenal syndrome (e.g., pulmonary renal syndrome), acidosis (e.g., renal tubular acidosis), nephropathy, and the like. The renal condition may be one that is induced by a trauma that results in the loss of kidney function or may be one that manifests as a result of an excessive retention of fluids and/or the retention of waste products, such as electrolytes e.g., nitrogen, sodium, potassium, calcium, etc. that build up to abnormally high levels within the kidneys and become toxic to the body. The renal condition may also be one that is induced by dehydration, decreased cardiac output, blood loss, and/or induced by the administration of various medications; such as contrast agents used in X-ray tests, non-steroidal anti-inflammatory drugs (NSAIDs), and antibiotics. In certain embodiments, the renal condition is associated with or otherwise manifested by an increase in a hormone level, such as an increase in renin, angiotensin, aldosterone, vasopressin, catecholamines, natriutic peptides, and the like, and treatment involves at least the reduction of the indicative hormone level. Other renal associated conditions may also be treated in accordance with the subject invention. Embodiments of the subject invention include treating one or more conditions, sequentially or at the same time, in accordance with the subject invention.

In representative embodiments, the target renal condition that is treated is one that results from maladaptive activation of the renal trauma response, (e.g., where the maladaptive response is to conserve hemodynamic volume by reducing urine output), where such conditions include, but are not limited to, maladaptive response conditions instigated by heart failure, aging, atherosclerosis, renal artery stenosis, diabetes, contrast agent induced nephropathy, The target renal conditions which are treated in certain embodiments of the invention include those that are readily identified using any convenient diagnostic measure. There are several different diagnostic measures that can be evaluated to determine if a subject's kidneys are functioning within healthy parameters. For instance, several different blood or urine related factors (such as electrolytes) or fluid build up (edema) may be measured. For example, serum or urine creatinine and urea nitrogen levels may be measured. Creatinine is a waste product that comes from normal wear and tear on muscles of the body. Urea nitrogen is a waste product produced by metabolism of protein. As kidney disease progresses, the levels of creatinine and urea nitrogen in the blood increases. Although healthy levels of creatinine and urea nitrogen will vary, appropriate ranges can easily be determined by one of ordinary skill in the art. Levels of creatinine will normally be in the range of about 0.5 to about 1.5 mg/dl, from about 0.75 to about 1.25 mg/dl, or about 1 mg/dl. Levels of urea nitrogen will normally be in the range of about 5 to about 25 mg/dl, from about 10 to about 20 mg/dl, or about 15 mg/dl. Therefore higher levels of creatinine may be a sign that the kidneys are not working properly and an evaluation of sympathetic bias may be made. An ultrasound of the kidneys and/or a measurement of kidney size may also help determine whether kidneys are functioning properly.

Accordingly, in certain embodiments, the renal condition to be treated is manifested by or otherwise associated with an increase in a hormone level, such as an increase in rennin, angiotensin, aldosterone, vasopressin, catecholamines, natriutic peptides, and the like, and treatment involves the reduction of the indicative hormone level.

A variety of subjects are treatable according to the subject methods. In many embodiments the subjects are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the subjects are humans.

In certain embodiments, the subject methods of modulation autonomic activity of the kidney are employed to treat non-renal conditions, e.g., conditions of other organs, where the non-renal conditions are impacted by the autonomic state of the kidney, where such conditions include, but are not limited to: cardio-renal conditions, hepatorenal conditions, pulmonary renal conditions, etc. In such applications, the autonomic nervous system of the kidney(s) is modulated in a manner effective to treat the non-renal condition. Representative conditions of interest include, but are not limited to: abnormalities in a subject's autonomic nervous system characterized by an abnormally high parasympathetic activity or abnormally low parasympathetic activity and/or an abnormally high sympathetic activity or abnormally low sympathetic activity. Examples of conditions that may be treated with the methods of the subject invention include, but are not limited to, cardiovascular diseases, e.g., atherosclerosis, coronary artery disease, hypertension, hyperlipidemia, cardiomyopathy, volume retention; neurodegenerative diseases, e.g., Alzheimer's disease, Pick's disease, dementia, delirium, Parkinson's disease, amyotrophic lateral sclerosis; neuroinflammatory diseases, e.g., viral meningitis, viral encephalitis, fungal meningitis, fungal encephalitis, multiple sclerosis, charcot joint; myasthenia gravis; orthopedic diseases, e.g., osteoarthritis, inflammatory arthritis, reflex sympathetic dystrophy, Paget's disease, osteoporosis; lymphoproliferative diseases, e.g., lymphoma, lymphoproliferative disease, Hodgkin's disease; autoimmune diseases, e.g., Graves disease, hashimoto's, takayasu's disease, kawasaki's diseases, arthritis, scleroderma, CREST syndrome, allergies, dermatitis, Henoch-schlonlein purpura, goodpasture syndrome, autoimmune thyroiditis, myasthenia gravis, Reiter's disease, lupus, rheumatoid arthritis; inflammatory and infectious diseases, e.g., sepsis, viral and fungal infections, wound healing, tuberculosis, infection, human immunodeficiency virus; pulmonary diseases, e.g., tachypnea, fibrotic diseases such as cystic fibrosis, interstitial lung disease, desquamative interstitial pneumonitis, non-specific interstitial pneumonitis, lymphocytic interstitial pneumonitis, usual interstitial pneumonitis, idiopathic pulmonary fibrosis; transplant-related side effects such as rejection, transplant-related tachycardia, renal failure, typhlitis; transplant related bowel dysmotility, transplant-related hyperreninemia; sleep disorders, e.g., insomnia, obstructive sleep apnea, central sleep apnea; gastrointestinal disorders, e.g., hepatitis, xerostomia, bowel dysmotility, peptic ulcer disease, constipation, post-operative bowel dysmotility; inflammatory bowel disease; endocrine disorders, e.g., hypothyroidism, hyperglycemia, diabetes, obesity, syndrome X; cardiac rhythm disorders, e.g., sick sinus syndrome, bradycardia, tachycardia, QT interval prolongation arrhythmias, atrial arrhythmias, ventricular arrhythmias; genitourinary disorders, e.g., bladder dysfunction, renal failure, hyperreninemia, hepatorenal syndrome, renal tubular acidosis, erectile dysfunction; cancer; fibrosis; skin disorders, e.g., wrinkles, cutaneous vasculitis, psoriasis; aging associated diseases and conditions, e.g., shy dragers, multi-system atrophy, osteoporosis, age related inflammation conditions, degenerative disorders; autonomic dysregulation diseases; e.g., headaches, concussions, post-concussive syndrome, coronary syndromes, coronary vasospasm; neurocardiogenic syncope; neurologic diseases such as epilepsy, seizures, stress, bipolar disorder, migraines and chronic headaches; conditions related to pregnancy such as amniotic fluid embolism, pregnancy-related arrhythmias, fetal stress, fetal hypoxia, eclampsia, preeclampsia; conditions that cause hypoxia, hypercarbia, hypercapnia, acidosis, acidemia, such as chronic obstructive lung disease, emphysema, cardiogenic pulmonary edema, non-cardiogenic pulmonary edema, neurogenic edema, pleural effusion, adult respiratory distress syndrome, pulmonary-renal syndromes, interstitial lung diseases, pulmonary fibrosis, and any other chronic lung disease; sudden death syndromes, e.g., sudden infant death syndrome, sudden adult death syndrome; vascular disorders, e.g., acute pulmonary embolism, chronic pulmonary embolism, deep venous thrombosis, venous thrombosis, arterial thrombosis, coagulopathy, aortic dissection, aortic aneurysm, arterial aneurysm, myocardial infarction, coronary vasospasm, cerebral vasospasm, mesenteric ischemia, arterial vasospasm, malignant hypertension; primary and secondary pulmonary hypertension, reperfusion syndrome, ischemia, cerebral vascular accident, cerebral vascular accident and transient ischemic attacks; pediatric diseases such as respiratory distress syndrome; bronchopulmonary dysplasia; Hirschprung disease; congenital megacolon, aganglionosis; ocular diseases such as glaucoma; and the like.

Additional conditions of interest that may be treated by embodiments of the subject methods include those described in U.S. patent application Ser. Nos. 10/661,368; 10/748,897; 10/748,976; 10/871,366; 10/846,486 10/917,270; 10/962,190 11/060,643 11/251,629; 11/238,108; 60/654,139 and 60/702,776; the disclosures of which are herein incorporated by reference.

Computer Readable Mediums and Programming Stored Thereon

The subject invention includes computer readable media having programming stored thereon for implementing the subject methods. For example, the subject invention may include suitable computing means such as suitable hardware/software for performing the subject methods.

In certain embodiments, programming may control a device to administer a pharmacological agent to a subject, e.g., programming may be configured to determine suitable dosage, etc. In certain embodiments programming may control a device to administer electrical energy to a subject, e.g., may control the activation/termination of electrical energy including selecting suitable electrical parameters. Programming may be configured to, or otherwise be capable of, directing a microprocessor to activate, i.e., turn "on" and "off" an electric energy applying device for applying energy to a subject. For example, if so determined, the processor may direct the electric energy applying device to provide the appropriate energy to result in the desired action. Accordingly, a processor may select the appropriate parameters (e.g., frequency, amplitude, etc.) depending on what is required and direct an electric energy applying device to implement the parameters.

Programming according to the subject invention may be recorded on computer-readable media, e.g., any medium that can be read and accessed directly or indirectly by a computer. Such media include, but are not limited to, computer disk or CD, a floppy disc, a magnetic "hard card", a server, magnetic tape, optical storage such as CD-ROM and DVD, electrical storage media such as RAM and ROM, and the hybrids of these categories such as magnetic/optical storage media. One of skill in the art can readily appreciate how any of the presently known computer readable mediums may be used to provide a manufacture that includes a recording of the present programming/algorithm for carrying out the above-described methodology. Thus, the computer readable media may be, for example, in the form of any of the above-described media or any other computer readable media capable of containing programming, stored electronically, magnetically, optically or by other means. As such, stored programming embodying steps for carrying-out some or all of the subject methods may be transferred to a computer-operated apparatus such as a personal computer (PC) or the like, by physical transfer of a CD, floppy disk, or like medium, or may be transferred using a computer network, server, or other interface connection, e.g., the Internet.

For example, the subject invention may include a computer readable medium that includes stored programming embodying an algorithm for carrying out the subject methods, where such an algorithm is used to direct a processor or series of processors to execute the steps necessary to perform the task(s) required of it and as such in certain embodiments the subject invention includes a computer-based system for carrying-out some or all of the subject methods. For example, such a stored algorithm may be configured to, or otherwise be capable of, directing a microprocessor to receive information directly or indirectly from data gathering means and process that information to determine if intervention is required. The result of that processing may be communicated to a user, e.g., via audio and/or visual means, e.g., the algorithm may also include steps or functions for generating a variety of profile graphs, plots, etc.

The subject invention may also include a data set of known or reference information stored on a computer readable medium to which data collected may be compared for use in determining a given treatment regimen. The data may be stored or configured in a variety of arrangements known to those of skill in the art.

Kits

Also provided are kits for practicing the subject methods. Kits may include one or more pharmacological agents, as described above. The dosage amount of the one or more pharmacological agents provided in a kit may be sufficient for a single application or for multiple applications. Accordingly, in certain embodiments of the subject kits a single dosage amount of a pharmacological agent is present and in certain other embodiments multiple dosage amounts of a pharmacological agent may be present in a kit. In those embodiments having multiple dosage amounts of pharmacological agent, such may be packaged in a single container, e.g., a single tube, bottle, vial, and the like, or one or more dosage amounts may be individually packaged such that certain kits may have more than one container of a pharmacological agent.

Suitable means for delivering one or more pharmacological agents to a subject may also be provided in a subject kit. The particular delivery means provided in a kit is dictated by the particular pharmacological agent employed, as describe above, e.g., the particular form of the agent such as whether the pharmacological agent is formulated into preparations in solid, semi-solid, liquid or gaseous forms, such as tablets, capsules, powders, granules, ointments, solutions, suppositories, injections, inhalants and aerosols, and the like, and the particular mode of administration of the agent, e.g., whether oral, buccal, rectal, parenteral, intraperiactivityal, intradermal, transdermal, intracheal, etc. Accordingly, certain systems may include a suppository applicator, syringe, I.V. bag and tubing, electrode, etc.

The subject kits may also include an electric energy applying device, as described above. Devices for delivering, e.g., implanting, an electric energy applying device to a target site of a subject such as into the body cavity of a subject may also be included in the subject kits. For example, an endoscope, introducer needle, and the like may be provided.

The subject kits may also include instructions for how to practice the subject methods using the components of the kit. The instructions may be recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Some or all components of the subject kits may be packaged in suitable packaging to maintain sterility. In many embodiments of the subject kits, the components of the kit are packaged in a kit containment element to make a single, easily handled unit, where the kit containment element, e.g., box or analogous structure, may or may not be an airtight container, e.g., to further preserve the sterility of some or all of the components of the kit.

EXPERIMENTAL

The following examples are put forth so as to provide those of ordinary skill in the art with a complete disclosure and description of how to make and use the present invention, and are not intended to limit the scope of what the inventors regard as their invention. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1 Intrarenal Administration of Metoprolol to Prevent Contrast Nephropathy Patients are prospectively enrolled on the basis of anticipated use of radiocontrast prior to a scheduled diagnostic coronary catherization. Treatment subjects are treated by intrarenal infusion of metoprolol 1 hour prior to the procedure. Subjects in the treatment group have a significant reduction in incidence of contrast nephropathy (as indicated by a greater than 25% increase in serum creatinine post-procedure) as compared to control.

Example 2. Intrarenal Administration of a Renin Inhibitor to Treat Hypertension

Patients are enrolled on the basis of a clinical diagnosis of hypertension based on serial systolic and diastolic blood pressure measurements by sphygmomanometer. Treatment subjects are treated by weekly infusions of Aliskiren via an intrarenal catheter. Control subjects have an intrarenal catheter placed but receive only saline infusions. Subjects in the treatment group hav a significant reduction in both systolic and diastolic blood pressure measurements compared to control.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of preventing contrast-induced nephropathy in a subject, said method comprising:
   evaluating the subject for sympathetic bias induced by administration of a contrast agent; and
   modulating at least one portion of the autonomic nervous system in said evaluated subject having sympathetic bias by selectively administering a beta blocker or a renin inhibitor to the kidney by intrarenal infusion, in a manner effective to prevent said contrast-induced nephropathy,
   wherein said modulating comprises increasing parasympathetic activity and decreasing the sympathetic bias in said subject to prevent contrast-induced nephropathy in said subject.

2. The method of claim 1, wherein said method further comprises at least applying electrical energy from an electrical energy applying device to said at least one portion of said autonomic nervous system.

3. The method of claim 2, wherein said method comprises increasing parasympathetic activity.

4. The method of claim 2, wherein said method comprises decreasing sympathetic activity.

5. The method of claim 2, wherein said method comprises increasing parasympathetic activity and decreasing sympathetic activity.

6. The method of claim 1, wherein said contrast-induced nephropathy is iodine-based contrast-induced nephropathy.

7. A computer-readable medium with stored programming embodying an algorithm for modulating at least one portion of the autonomic nervous system of a subject in accordance with the method of claim 1.

8. A system comprising:
   (a) a computer-readable medium with stored programming embodying an algorithm-for modulating at least one portion of the autonomic nervous system of a subject according to a method of claim 1;
   (b) an effective amount of the pharmacological agent, and
   (c) a drug delivery device.

9. A kit comprising:
   a pharmacological agent; and
   instructions for administering said pharmacological agent to a subject according to the method of claim 1; and
   a drug delivery device for selectively administering said pharmacological agent to a kidney by intrarenal infusion, wherein the pharmacological agent is a beta blocker or a renin inhibitor.

10. The method according to claim 1, wherein said modulating further comprises increasing said parasympathetic activity in said subject to result in parasympathetic bias in said portion of the autonomic nervous system.

11. The method of claim 1, wherein the pharmacological agent is a renin inhibitor and the renin-inhibitor is aliskiren.

12. The method of claim 11, wherein said aliskiren is administered by weekly infusion.

13. The kit of claim 9, wherein the pharmacological agent is a beta blocker and the beta blocker is metoprolol.

14. The method of claim 1, wherein the pharmacological agent is a beta blocker.

15. The method of claim 14, wherein the beta blocker is metoprolol.

16. The method of claim 1, wherein modulating at least one portion of the autonomic nervous system in said evaluated subject having sympathetic bias comprises selectively administering a beta blocker to the kidney by intrarenal infusion, in a manner effective to prevent said contrast-induced nephropathy.

17. The method according to claim 16, wherein the beta blocker is the sole active agent selectively administered to the kidney to modulate the at least one portion of the autonomic nervous system and prevent the contrast-induced nephropathy.

18. The method of claim 1, wherein modulating at least one portion of the autonomic nervous system in said evaluated subject having sympathetic bias comprises selectively administering a renin inhibitor to the kidney by intrarenal infusion, in a manner effective to prevent said contrast-induced nephropathy.

19. The method according to claim 18, wherein the renin inhibitor is the sole active agent selectively administered to the kidney to modulate the at least one portion of the autonomic nervous system and prevent the contrast-induced nephropathy.

* * * * *